(12) United States Patent
Kao et al.

(10) Patent No.: US 10,202,342 B2
(45) Date of Patent: Feb. 12, 2019

(54) TARGETED DELIVERY OF IMAGING PROBES FOR IN VIVO CELLULAR IMAGING

(75) Inventors: Joseph P. Y. Kao, Silver Spring, MD (US); Scott R. Burks, Baltimore, MD (US); Gerald R. Rosen, Rockville, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 1586 days.

(21) Appl. No.: 12/975,655

(22) Filed: Dec. 22, 2010

(65) Prior Publication Data

US 2011/0165087 A1    Jul. 7, 2011

Related U.S. Application Data

(63) Continuation-in-part of application No. PCT/US2009/049023, filed on Jun. 29, 2009.

(60) Provisional application No. 61/076,485, filed on Jun. 27, 2008.

(51) Int. Cl.
```
C07D 207/46     (2006.01)
A61K 49/00      (2006.01)
A61K 49/10      (2006.01)
A61K 49/18      (2006.01)
A61K 49/20      (2006.01)
C07D 211/94     (2006.01)
C07D 403/06     (2006.01)
A61B 5/055      (2006.01)
G01N 33/542     (2006.01)
G01N 33/543     (2006.01)
G01N 33/574     (2006.01)
G01R 33/60      (2006.01)
A61B 5/00       (2006.01)
```

(52) U.S. Cl.
CPC ............ *C07D 207/46* (2013.01); *A61B 5/055* (2013.01); *A61K 49/0041* (2013.01); *A61K 49/0084* (2013.01); *A61K 49/10* (2013.01); *A61K 49/1812* (2013.01); *A61K 49/20* (2013.01); *C07D 211/94* (2013.01); *C07D 403/06* (2013.01); *G01N 33/542* (2013.01); *G01N 33/5432* (2013.01); *G01N 33/54353* (2013.01); *G01N 33/574* (2013.01); *G01R 33/60* (2013.01); *A61B 5/0071* (2013.01); *C07B 2200/05* (2013.01)

(58) Field of Classification Search
CPC ........ A61K 49/20; A61K 9/127; A61K 31/40; A61K 49/1812; A61K 49/0041; A61K 49/0084; A61K 49/10; A61B 5/055; A61B 5/0071; C07D 207/46; C07D 211/94; C07D 403/06; G01N 33/542; G01N 33/5432; G01N 33/54353; G01N 33/574; G01R 33/60; C07B 2200/05

USPC ......................... 424/9.3, 9.33, 450
See application file for complete search history.

(56) References Cited

U.S. PATENT DOCUMENTS

| | | | |
|---|---|---|---|
| 4,834,964 A * | 5/1989 | Rosen | 424/9.33 |
| 4,845,090 A * | 7/1989 | Gries | A61K 49/20 |
| | | | 424/9.33 |
| 5,104,641 A * | 4/1992 | Rosen | A61K 49/20 |
| | | | 424/9.33 |
| 5,725,839 A | 3/1998 | Hsia | |
| 2005/0112065 A1 * | 5/2005 | Drummond et al. | 424/9.321 |

OTHER PUBLICATIONS

Miyake et al., J. Pharmacol. and Exper. Therapeutics, 2006, 318(3), p. 1187-1193).*
Humphries et al., Proc. Nat. Acac. Sci. USA, 1974, 71(5), p. 1691-1694.*
Utsumi et al., PNAS, 2006, 103(5), p. 1463-1468.*
Utsumi et al., PNAS, 2006, 103(5), p. 1463-1468 (abstract).*
Noble, O.C. et al. "Development of ligand-targeted liposomes for cancer therapy." Expert Opinion on Therapeutic Targets. Aug. 2004, vol. 8. No. 4. Abstract.
Yokoyama, H. et al. "EPR Imaging for in vivo analysis of the half-life of a nitroxide radical in the hippocampus and cerebral cortex of rats after epileptic seizures." Free Radical Biology & Medicine. 1999, vol. 27, No. 3/4, pp. 442-448.
Samuni, A.M. et al. "Site-activity relationship of nitroxide radical's antioxidative effect." Free Radical Biology & Medicine, 2003, vol. 34, No. 2, pp. 177-185.
Sauer, I. et al. "Dipalmitoylation of a cellular uptake-mediating apolipoprotein E-derived peptide as a promising modification for stable anchorage in liposomal drug carriers." Biochimica et Biophysica Acta. 2006, pp. 552-561.
Allen TM, Cheng WW, Hare JI, Laginha KM (2006) Pharmacokinetics and pharmacodynamics of lipidic nano-particles in cancer. *Anticancer Agents Med Chem* 6: 513-23.
Baselga J, Albanell J, Molina MA, Arribas J (2001) Mechanism of action of trastuzumab and scientific update. *Semin Oncol* 28: 4-11.
Burks SR, Barth ED, Halpern HJ, Rosen GM, Kao JP (2009) Targeted delivery of electron paramagnetic resonance imaging probes through endocytosis of liposomes. *Biochim Biophys Acta*: Oct. 2009, 1788(10): 2301-2308.
Charrois GJ, Allen TM (2003) Rate of biodistribution of STEALTH liposomes to tumor and skin: influence of liposome diameter and implications for toxicity and therapeutic activity. *Biochim Biophys Acta* 1609: 102-8.

(Continued)

*Primary Examiner* — Michael G. Hartley
*Assistant Examiner* — Leah H Schlientz
(74) *Attorney, Agent, or Firm* — Tristan A. Fuierer; Marianne Fuierer; Olive Law Group, PLLC

(57) ABSTRACT

The present invention relates to nitroxide imaging probes that are isotopically modified or unmodified. Such nitroxide imaging probes may be included in liposomes that encapsulate self-quenching concentrations thereof, wherein the liposomes optionally comprise a targeting ligand specific to and having affinity for targeted tissue.

8 Claims, 23 Drawing Sheets

(56) References Cited

OTHER PUBLICATIONS

Chen TJ, Cheng TH, Chen CY, Hsu SC, Cheng TL, Liu GC, Wang YM (2009) Targeted Herceptin-dextran iron oxide nanoparticles for noninvasive imaging of HER2/neu receptors using MRI. *J Biol Inorg Chem* 14: 253-60.
Dreher MR, Elas M, Ichikawa K, Barth ED, Chilkoti A, Rosen GM, Halpern HJ, Dewhirst M (2004) Nitroxide conjugate of a thermally responsive elastin-like polypeptide for noninvasive thermometry. *Med Phys* 31: 2755-62.
Elas M, Ahn KH, Parasca A, Barth ED, Lee D, Haney C, Halpern HJ (2006) Electron paramagnetic resonance oxygen images correlate spatially and quantitatively with Oxylite oxygen measurements. *Clin Cancer Res* 12: 4209-4217.
Elas M, Bell R, Hleihel D, Barth ED, McFaul C, Haney CR, Bielanska J, Pustelny K, Ahn KH, Pelizzari CA, Kocherginsky M, Halpern HJ (2008) Electron paramagnetic resonance oxygen image hypoxic fraction plus radiation dose strongly correlates with tumor cure in FSa fibrosarcomas. *Int J Radiat Oncol Biol Phys* 71: 542-549.
Halpern HJ, Chandramouli GV, Barth ED, Yu C, Peric M, Grdina DJ, Teicher BA (1999) Diminished aqueous microviscosity of tumors in murine models measured with in vivo radiofrequency electron paramagnetic resonance. *Cancer Res* 59: 5836-5841.
Halpern HJ, Spencer DP, Vanpolen J, Bowman MK, Nelson AC, Dowey EM, Teicher BA (1989) Imaging radio-frequency electron-spin-resonance spectrometer with high-resolution and sensitivity for in vivo measurements. *Review of Scientific Instruments* 60: 1040-1050.
Kallioniemi OP, Kallioniemi A, Kurisu W, Thor A, Chen LC, Smith HS, Waldman FM, Pinkel D, Gray JW (1992) ERBB2 amplification in breast cancer analyzed by fluorescence in situ hybridization. *Proc Natl Acad Sci U S A* 89: 5321-5.
Kao JP, Barth ED, Burks SR, Smithback P, Mailer C, Ahn KH, Halpern HJ, Rosen GM (2007) Very-low-frequency electron paramagnetic resonance (EPR) imaging of nitroxide-loaded cells. *Magn Reson Med* 58: 850-4.
Khramtsov VV, Weiner LM, Grigoriev IA, Volodarsky LB (1982) Proton exchange in stable nitroxyl radicals. EPR study of the pH of aqueous solutions. *Chem Phys Lett*: 69-72.
King CR, Kraus MH, Aaronson SA (1985) Amplification of a novel v-erbB-related gene in a human mammary carcinoma. *Science* 229: 974-6.
Kirpotin DB, Drummond DC, Shao Y, Shalaby MR, Hong K, Nielsen UB, Marks JD, Benz CC, Park JW (2006) Antibody targeting of long-circulating lipidic nanoparticles does not increase tumor localization but does increase internalization in animal models. *Cancer Res* 66: 6732-40.
Kraus MH, Popescu NC, Amsbaugh SC, King CR (1987) Overexpression of the EGF receptor-related proto-oncogene erbB-2 in human mammary tumor cell lines by different molecular mechanisms. *EMBO J* 6: 605-10.
Liu F, Liu D (1996) Serum independent liposome uptake by mouse liver. *BiochimBiophysActa* 1278: 5-11.
Mamot C, Drummond DC, Greiser U, Hong K, Kirpotin DB, Marks JD, Park JW (2003) Epidermal growth factor receptor (EGFR)-targeted immunoliposomes mediate specific and efficient drug delivery to EGFR- and EGFRvIII-overexpressing tumor cells. *Cancer Res* 63: 3154-61.
Marx D, Schauer A, Reiche C, May A, Ummenhofer L, Reles A, Rauschecker H, Sauer R, Schumacher M (1990) c-erbB2 expression in correlation to other biological parameters of breast cancer. *J Cancer Res Clin Oncol* 116: 15-20.
Ogawa M, Kosaka N, Choyke PL, Kobayashi H (2009) In vivo molecular imaging of cancer with a quenching near-infrared fluorescent probe using conjugates of monoclonal antibodies and indocyanine green. *Cancer Res* 69: 1268-72.
Orlova A, Wallberg H, Stone-Elander S, Tolmachev V (2009) On the selection of a tracer for PET imaging of HER2-expressing tumors: direct comparison of a 124I-labeled affibody molecule and trastuzumab in a murine xenograft model. *J Nucl Med* 50: 417-25.
Park JW, Hong K, Kirpotin DB, Colbern G, Shalaby R, Baselga J, Shao Y, Nielsen UB, Marks JD, Moore D, Papahadjopoulos D, Benz CC (2002) Anti-HER2 immunoliposomes: enhanced efficacy attributable to targeted delivery. *Clin Cancer Res* 8: 1172-81.
Park JW, Kirpotin DB, Hong K, Shalaby R, Shao Y, Nielsen UB, Marks JD, Papahadjopoulos D, Benz CC (2001) Tumor targeting using anti-her2 immunoliposomes. *J Control Release* 74: 95-113.
Rosen GM, Burks SR, Kohr MJ, Kao JP (2005) Synthesis and biological testing of aminoxyls designed for long-term retention by living cells. *Org Biomol Chem* 3: 645-8.
Sauer, I. et al. Dipalmitoylation of a cellular uptake-mediating apolipoprotein E-derived peptide as a promising modification for stable anchorage in liposomal.
Schmitz KR, Ferguson KM (2009) Interaction of antibodies with ErbB receptor extracellular regions. *Exp Cell Res* 315: 659-70.
Shen J, Liu S, Miyake M, Liu W, Pritchard A, Kao JPY, Rosen GM, Tong Y and Liu KJ (2006) Use of 3-acetoxymethoxycarbonyl-2,2,5,5-tetramethyl-1-pyrrolidinyloxyl as an EPR oximetry probe: Potential for in vivo measurement of tissue oxygenation in mouse brain. *Magn Reson Med* 55:1433-40.
Shepard HM, Lewis GD, Sarup JC, Fendly BM, Maneval D, Mordenti J, Figari I, Kotts CE, Palladino MA, Jr., Ullrich A, et al. (1991) Monoclonal antibody therapy of human cancer: taking the HER2 protooncogene to the clinic. *J Clin Immunol* 11: 117-27.
Slamon DJ, Clark GM, Wong SG, Levin WJ, Ullrich A, McGuire WL (1987) Human breast cancer: correlation of relapse and survival with amplification of the HER-2/neu oncogene. *Science* 235: 177-82.
Sliwkowski MX, Lofgren JA, Lewis GD, Hotaling TE, Fendly BM, Fox JA (1999) Nonclinical studies addressing the mechanism of action of trastuzumab (Herceptin). *Semin Oncol* 26: 60-70.
Szollosi J, Balazs M, Feuerstein BG, Benz CC, Waldman FM (1995) ERBB-2 (HER2/neu) gene copy number, p185HER-2 overexpression, and intratumor heterogeneity in human breast cancer. *Cancer Res* 55: 5400-7.
Utsumi H, Yamada K, Ichikawa K, Sakai K, Kinoshita Y, Matsumoto S, Nagai M (2006) Simultaneous molecular imaging of redox reactions monitored by Overhauser-enhanced MRI with 14N- and 15N-labeled nitroxyl radicals. *Proc Natl Acad Sci USA* 103: 1463-1468.
Woodle MC, Lasic DD (1992) Sterically stabilized liposomes. *BiochimBiophysActa* 1113: 171-199.
Yarden Y (2001) Biology of HER2 and its importance in breast cancer. *Oncology* 61 Suppl 2: 1-13.

\* cited by examiner

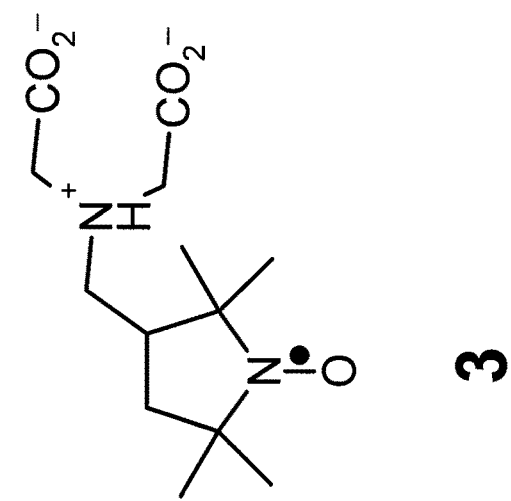
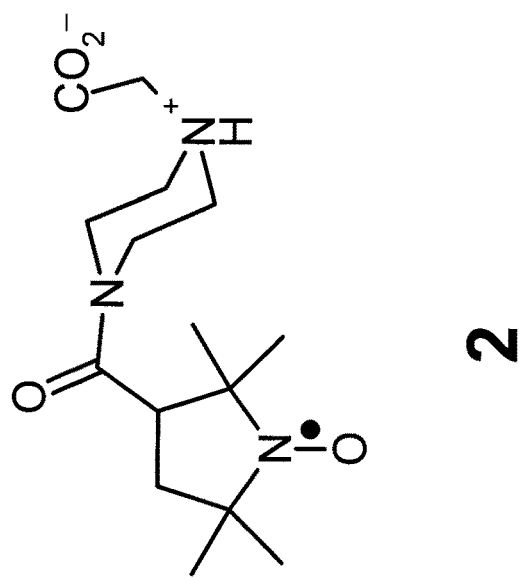
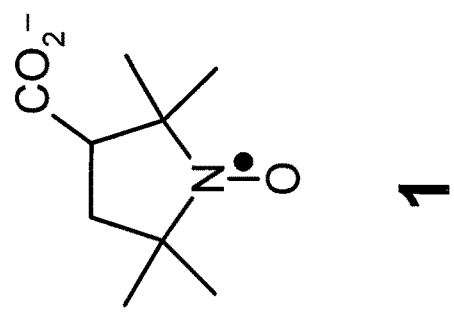
Figure 1

TARGETED DELIVERY OF IMAGING PROBES FOR IN VIVO CELLULAR IMAGING

CROSS-REFERENCE TO RELATED APPLICATIONS

The present application is a Continuation-in-Part Application of and claims priority to PCT International Application No. PCT/US2009/049023 filed on Jun. 29, 2009 which in turn claims priority to U.S. Provisional Patent Application No. 61/076,485 filed on Jun. 27, 2008, the contents of both applications are hereby incorporated by reference herein.

STATEMENT AS TO FEDERALLY SPONSORED RESEARCH

This invention was made with Government support under GM-056481 and EB-2034 awarded by National Institutes of Health. The Government has certain rights in the invention.

BACKGROUND OF THE INVENTION

Field of Invention

The present invention relates to detection probes and methods of use, and more particularly, stable free-radical probes (such as nitroxides) for use as contrast agents. The probes are optionally encapsulated in liposomes that are optionally targeted for specific binding sites on targeted tissue with a targeting ligand.

Description of the Related Art

Clinicians are concerned with detecting the presence of, and quantitatively measuring, a variety of substances via the use of many different analytical techniques. The most commonly used techniques employ absorbtiometry, both at visible and ultraviolet wavelengths; however, emission, flame photometry and radioactivity are also commonly used. Analyses based on the measurement of emitted light offer several distinct advantages over conventionally employed techniques, including high sensitivity, wide linear range, low cost per test, and relatively simple and inexpensive equipment.

The ability to label a specific cell type and image its presence, growth and/or movement in vivo, noninvasively and in real time would be of great importance in understanding the interactions of cells that regulate a spectrum of human physiology and in the diagnosis and evaluation of human diseases. Further, longer term imaging of tumor cells could, likewise, permit long-term studies of metastases.

In recent years, magnetic resonance imaging (MRI) with contrast media has been used to study a variety of important physiological processes. However, with the development of low-frequency electron paramagnetic resonance (EPR) spectrometers capable of detecting paramagnetic species in living animals in real time, EPR imaging is now an alternative technology that can, like MRI, address significant physiological questions. The challenge, however, has been the synthesis of paramagnetic spin probes that can provide these essential data and targeting of same to specific cells or aberrant tissue that is physiologically distinguishable from normal tissue.

It is, therefore, an object of the present invention to provide for a system for the detection of biological cells or tissues of interest, comprising a nitroxide or trityl stable free radical imaging probe that may optionally be encapsulated within a liposome, wherein the liposome may optionally be conjugated to targeting ligand specific to biological cells or tissues of interest.

SUMMARY OF THE INVENTION

In one aspect, the present invention relates to nitroxide imaging probes that are isotopically modified or unmodified. Such nitroxide imaging probes may be included in immunoliposomes that encapsulate self-quenching concentrations thereof, wherein the immunoliposomes comprise a targeting ligand specific to and have affinity for targeted tissue.

In another aspect the present invention relates to an imaging complex for identifying targeted tissue of interest, the imaging complex comprising:
a. a liposome;
b. a detection probe encapsulated within the liposome, wherein the detection probe is concentrated to a level causing self quenching with no or minimal identifiable signal; and
c. a targeting ligand positioned on the surface of the liposome and having affinity for a receptor on the targeted tissue of interest, and wherein the detection probe is a nitroxide or a triarylmethyl (trityl) radical, or a precursor or derivative thereof.

The present invention comprises the use of stable nitroxides, triarylmethyl (trityl) radicals, precursors and derivatives thereof for the detection probe. A nitroxide free radical is preferable, whose structure contains at least one nitroxide function, and may include, but is not limited to, the following compounds:

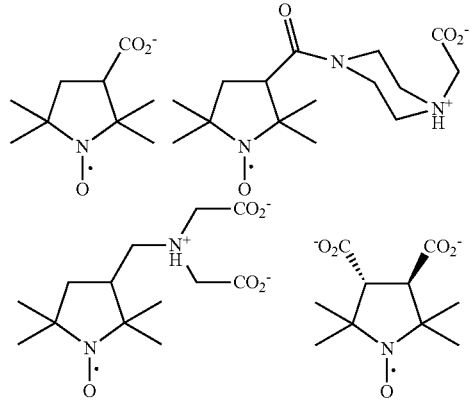

Triarylmethyl (trityl) radicals may include the following structure

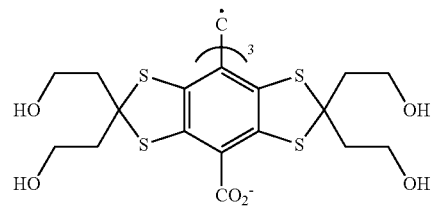

Trityl radical Ox063

Nitroxides or trityl radicals are detectable by EPR spectroscopy. With the development of advanced EPR imaging instrumentation, EPR images of intact biological tissues and organs are available based on a measurement and detection of the stable free radical. Pursuant to this invention, nitroxide or trityl radical levels in the targeted tissue may be maintained for a prolonged period of time allowing both improved image contrast and longer signal persistence.

A further aspect of the present invention relates to optimizing nitroxides that provide for longer cellular retention times, greater resolution, wherein isotopic substitutions are included in the nitroxides including replacing $^{14}$N with $^{15}$N and $^{1}$H with $^{2}$H (D) to provide for narrower linewidth and increased peak height in the detected signal. Those skilled in the art can synthesize other $^{15}$N and D-containing nitroxides, similar to the structure shown below, to provide narrow EPR spectral linewidths, and thus, enhance the EPR image in the cell or tissue of interest. Applicable isotopic nitroxides include, but are not limited to, the following compounds:

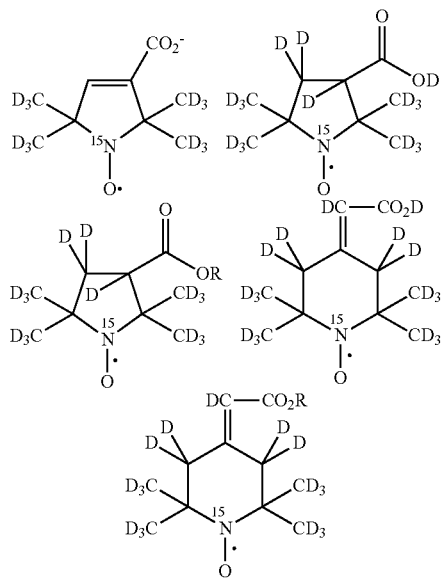

wherein R is $CH_2O_2C$—R', where R' is an alkyl group, containing 1 to 5 carbon atoms, more preferably 2 to 5 carbon atoms; e.g., R can be $CH_2O_2CCH_2CH_3$; $CH_2O_2C(CH_2)_3CH_3$; $CH_2O_2CCH_2CH(CH_3)_2$; $CH_2O_2C(CH_3)_3$; or $CH_2O_2C(CH_2)_5CH_3$. These isotopic nitroxides may be included in a liposome but also may be delivered without inclusion in a liposome and introduced by other acceptable modes of administration, such as injection or oral.

Yet another aspect of the present invention relates to a method of diagnosing the presence of diseased tissue/cells in a patient comprising:
 a. preparing a liposome having positioned on its surface a targeting ligand having affinity for the targeted tissue/cells of interest and a nitroxide or a trityl radical incorporated into interior phase of the liposome in an amount sufficient to cause a quenching of a detectable spectra signal, wherein the nitroxide or trityl radical may be isotopically modified or unmodified;
 b. administering the liposome to the patient, wherein the liposome is endocytosed and lysed in the tissue/cells to liberate the nitroxide or trityl radical;
 c. scanning the patient using a magnetic field; and
 d. determining the de-quenched spectral signal of the nitroxide or trityl radical loaded into the tissue/cells of interest.

For example, the patient can be a human or non-human animal.

In yet another aspect, the present invention relates to an immunoassay method for detecting or quantifying a targeted tissue of interest in a test fluid, said method comprising:
 a. forming a liposome having positioned on its surface a targeting ligand having affinity for a first area on the targeted tissue of interest and a nitroxide or trityl radical incorporated into interior phase thereof of the liposome, wherein the nitroxide or trityl radical is in an amount sufficient to cause a quenching of a detectable spectral signal until lysing of the liposome, wherein the nitroxide or trityl radical may be isotopically modified or unmodified;
 b. providing a solid phase inert support having attached thereto a support binding receptor having affinity for a second area on the tissue of interest, wherein the support binding receptor has no affinity for the targeting ligand of the liposome;
 c. mixing said test fluid with said receptor-solid phase support of step (b) for sufficient time to saturate said support binding receptor with any tissue of interest present in said test fluid;
 d. mixing said liposome formed in step (a) with said saturated receptor-solid phase support from step (c) and for binding with the first area on the targeted tissue of interest;
 e. causing the lysis of said liposome; and;
 f. scanning the support with a magnetic field to determine the presence of the nitroxide or trityl radical released by the liposome in step (e) and correlating said signal with the presence of the targeted tissue in the sample.

Another aspect relates to a method of providing an EPR image of a region of a patient, the method comprising:
 a. administering to the patient a liposome having positioned on its surface a targeting ligand having affinity for the targeted cell of interest and a nitroxide or trityl radical incorporated within the interior phase thereof of the liposome, wherein the nitroxide or trityl radical is in an amount sufficient to cause a quenching of a detectable spectral signal until lysing of the liposome in the patient, wherein the nitroxide or trityl radical may be isotopically modified or unmodified; and
 b. scanning the patient using a magnetic field wherein signals resonating from the tissue provide visible images of the tissue of the patient.

For example, the patient can be a human or non-human animal.

These and other aspects and advantages of the invention are evident in the description which follows and in the accompanying drawings.

BRIEF DESCRIPTION OF THE DRAWINGS

FIG. 1 shows three nitroxides for use in EPR imaging that can be easily incorporated into the immunoliposomes of the present invention.

Surface intensity plot of the cylinder with cross-sectional planes shown in gray. (B-D) Cross-sectional views of the cylinder at the planes are shown in panel A. All axis labels are in units of cm. Intensity is encoded according to the pseudogray scale shown at right.

Figure 7:
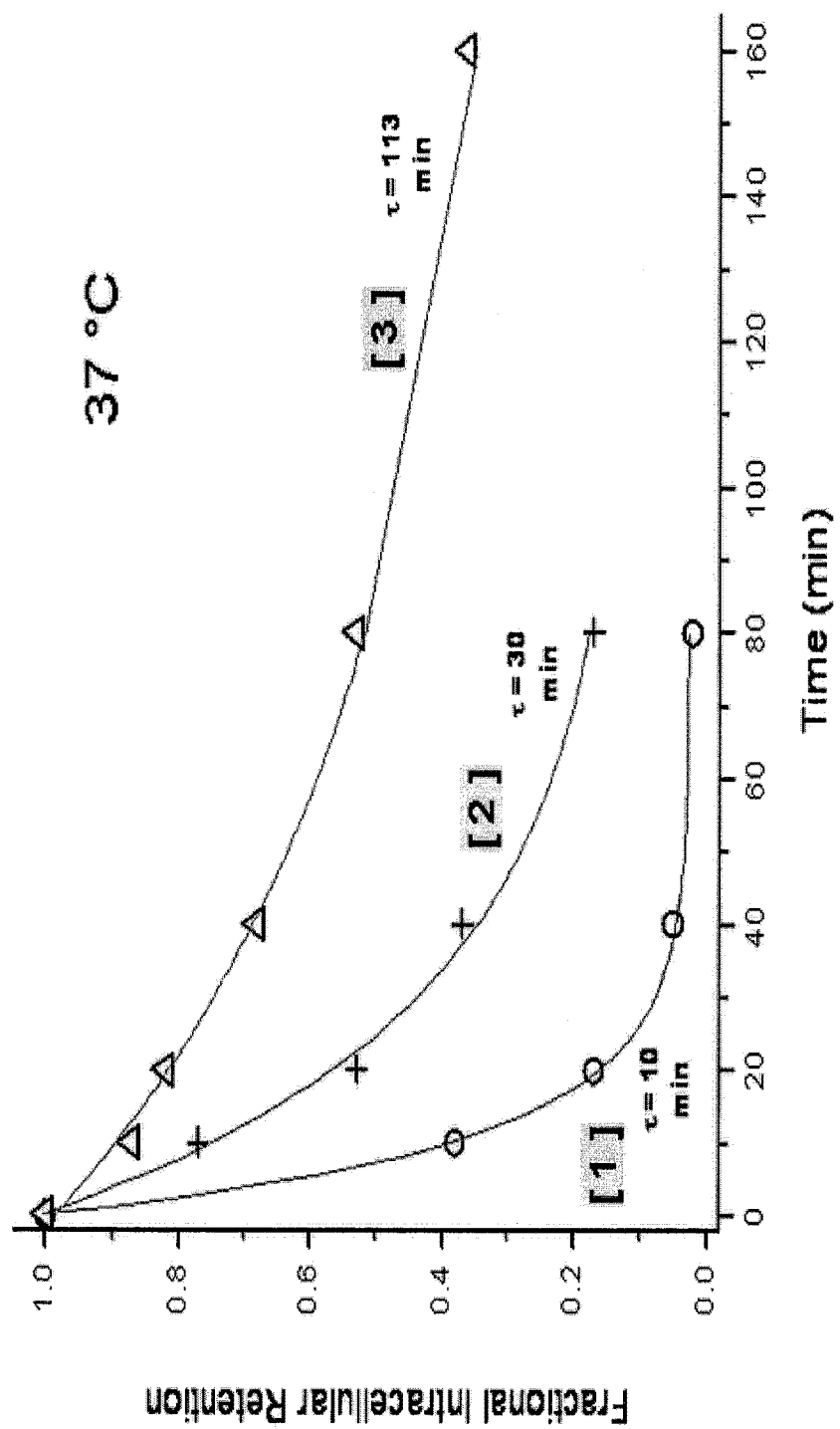

FIG. 7 shows the intracellular retention of nitroxides and the intracellular retention lifetimes determined from single-exponential fits of the data showing that nitroxide [3] has the longest life time within the cells. The exponential life time ($\tau$) is related to the half-life ($t^{1/2}$): $t^{1/2}=0.693\tau$.

Figure 8:
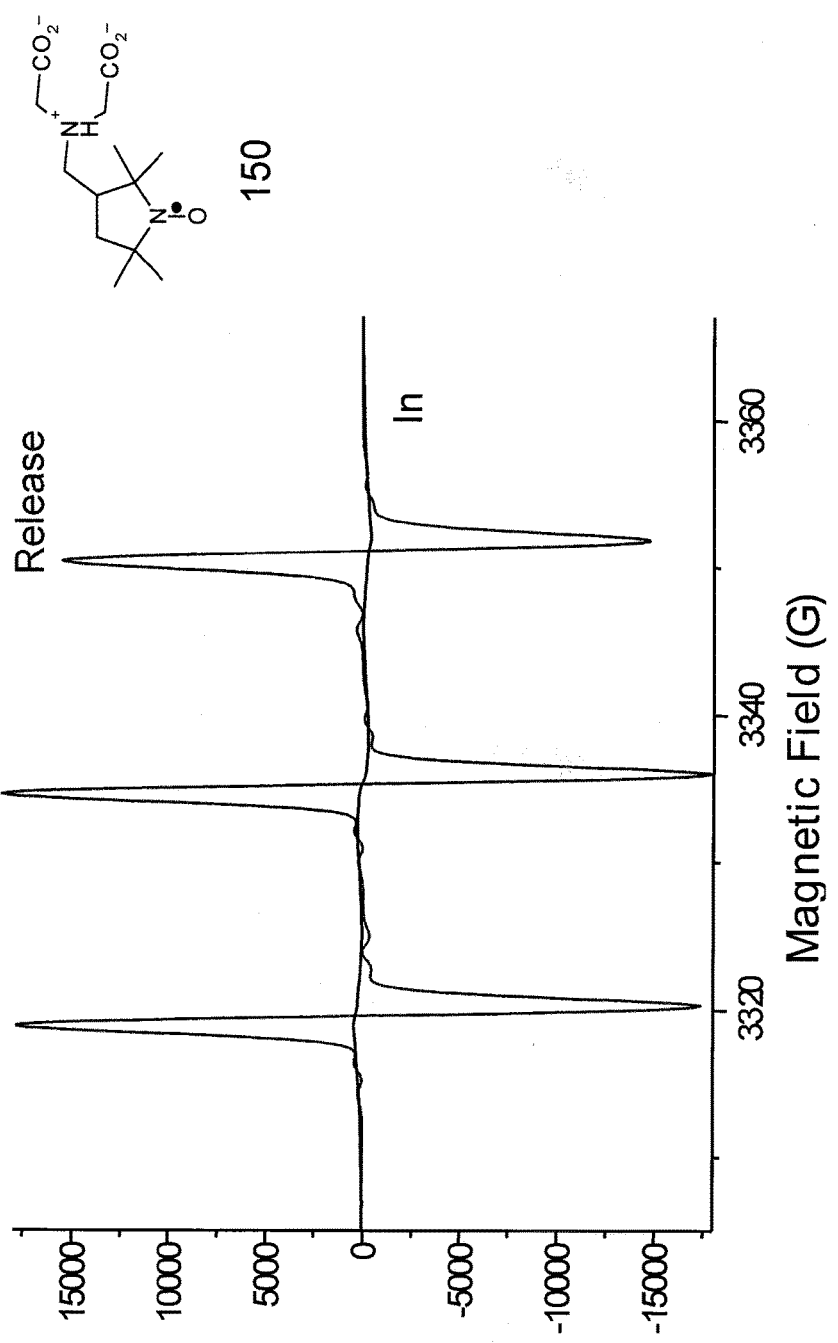

FIG. 8 shows the EPR signal for nitroxides contained in the liposome (essentially straight line) and the three peak signal when the liposome was lysed and the nitroxide was free to provide an EPR spectral signal. Thus, within the liposome, there is a very weak signal due to quenching at a high concentration of nitroxides but once released into the bulk solution, the concentration is diluted and de-quenching occurs with an increased signal.

Figure 9:
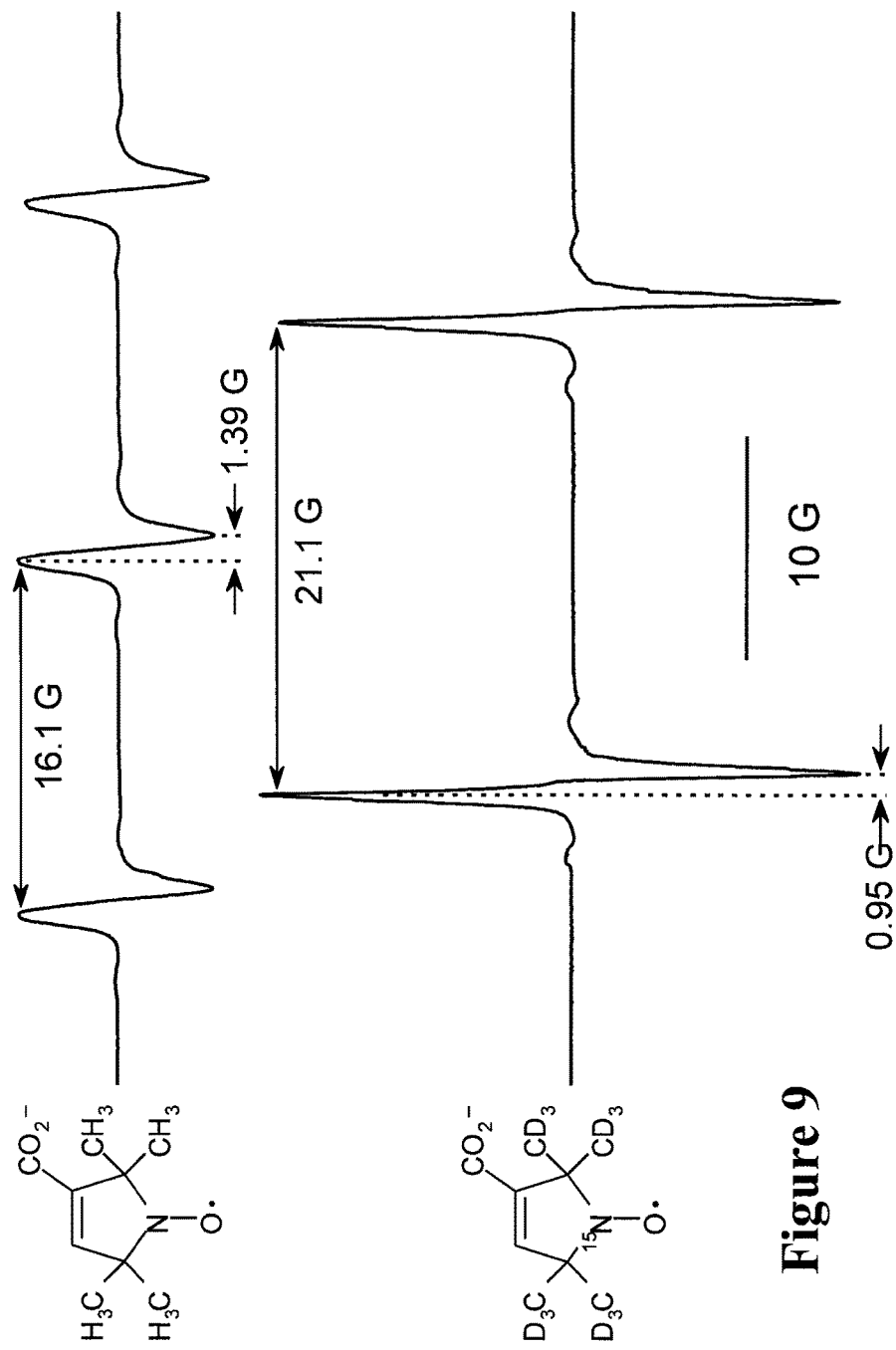

FIG. 9 shows the change in EPR spectral peaks with isotopic substitutions in nitroxides wherein substituted nitroxides have narrower spectral peaks and, as a result, larger peak amplitudes.

Figure 10:
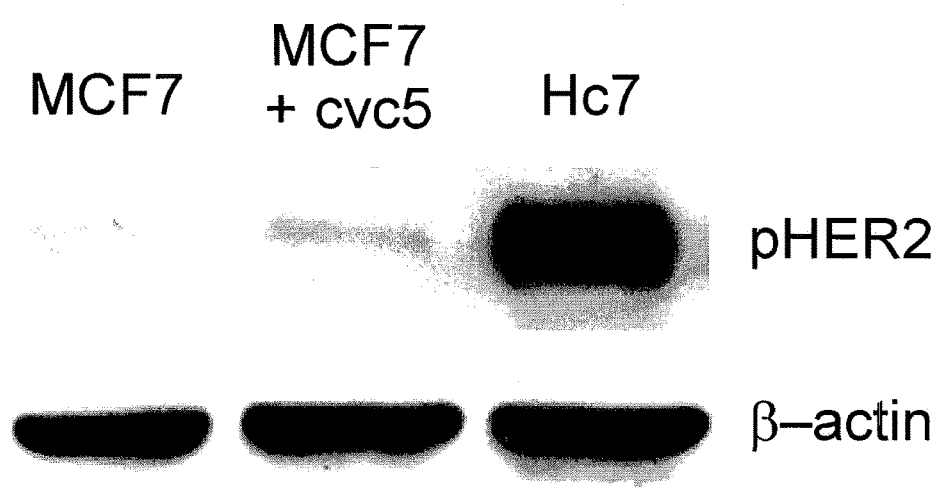

FIG. 10 shows western blots for HER2. Top row: Hc7 cell lysates show high expression of phospho-HER2 compared to untransfected MCF7 cells or MCF7 cells transfected with the cvc5 vector, which lacks HER2 DNA. Bottom row: β-actin staining as loading control.

Figure 11:
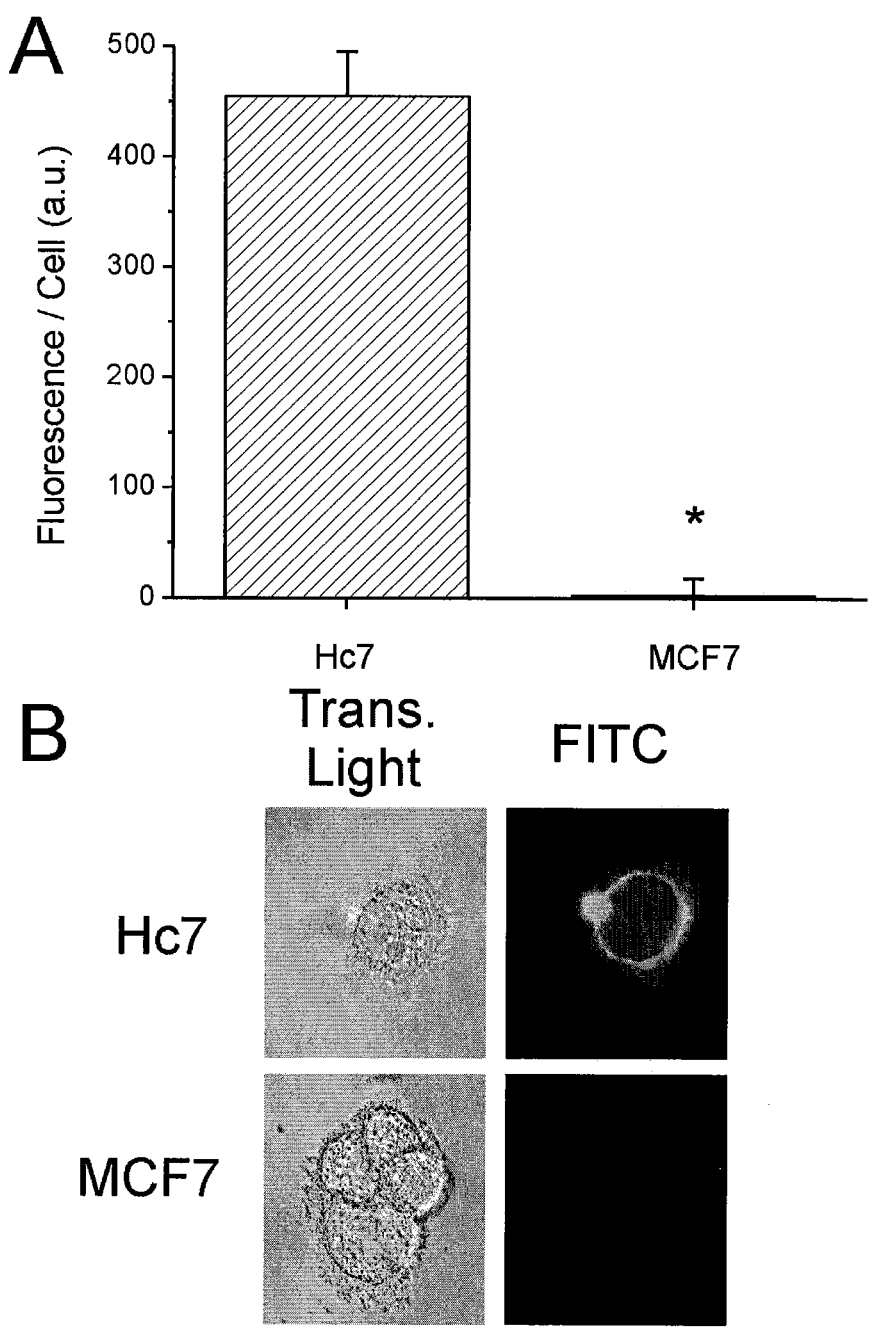

FIG. 11 shows the difference in expression of HER2 on the surface of Hc7 cells and MCF7 cells. Cells were fixed with paraformaldehyde (pH 7.4) in the absence of detergents. Trastuzumab was used as the primary antibody, with a human-Fab-specific, FITC-conjugated secondary antibody. A) Average FITC fluorescence is ~25-200× greater per Hc7 cell compared to the parent MCF7 line (error bars represent S.E.M., p<0.01). B) Representative brightfield and fluorescent images for Her2-stained Hc7 and MCF7 cells.

Figure 12:
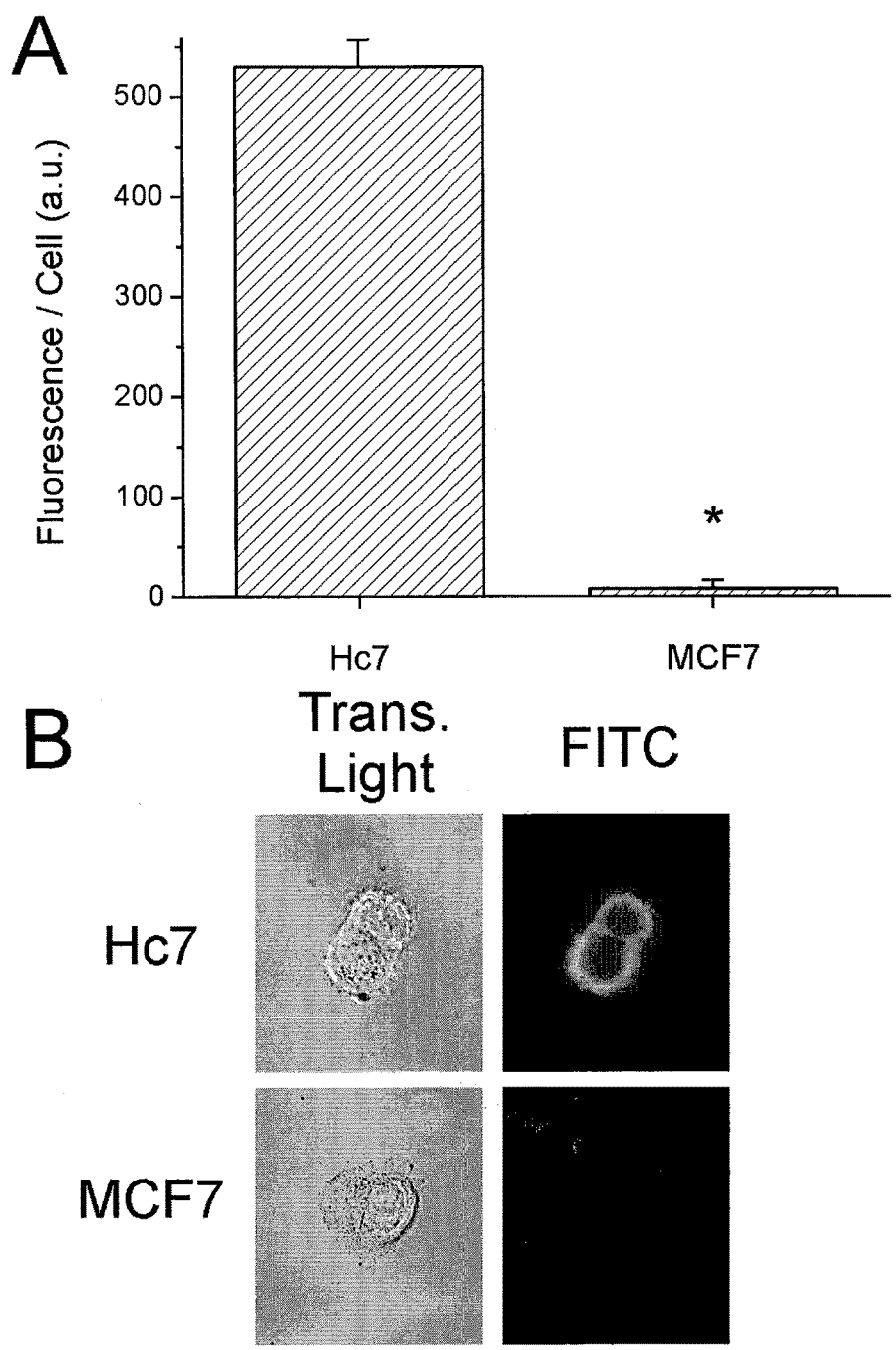

FIG. 12 shows that Trastuzumab Fab' fragments retain selective immunoreactivity with Her2. Primary staining was done with maleimide-inactivated trastuzumab Fab' fragments using the same protocol in FIG. 11. A) Average FITC fluorescence is ~35-70× greater per Hc7 cell compared to the parent MCF7 line (error bars represent S.E.M., p<0.01). B) Representative brightfield and fluorescent images for HER2-stained Hc7 and MCF7 cells.

Figure 13:
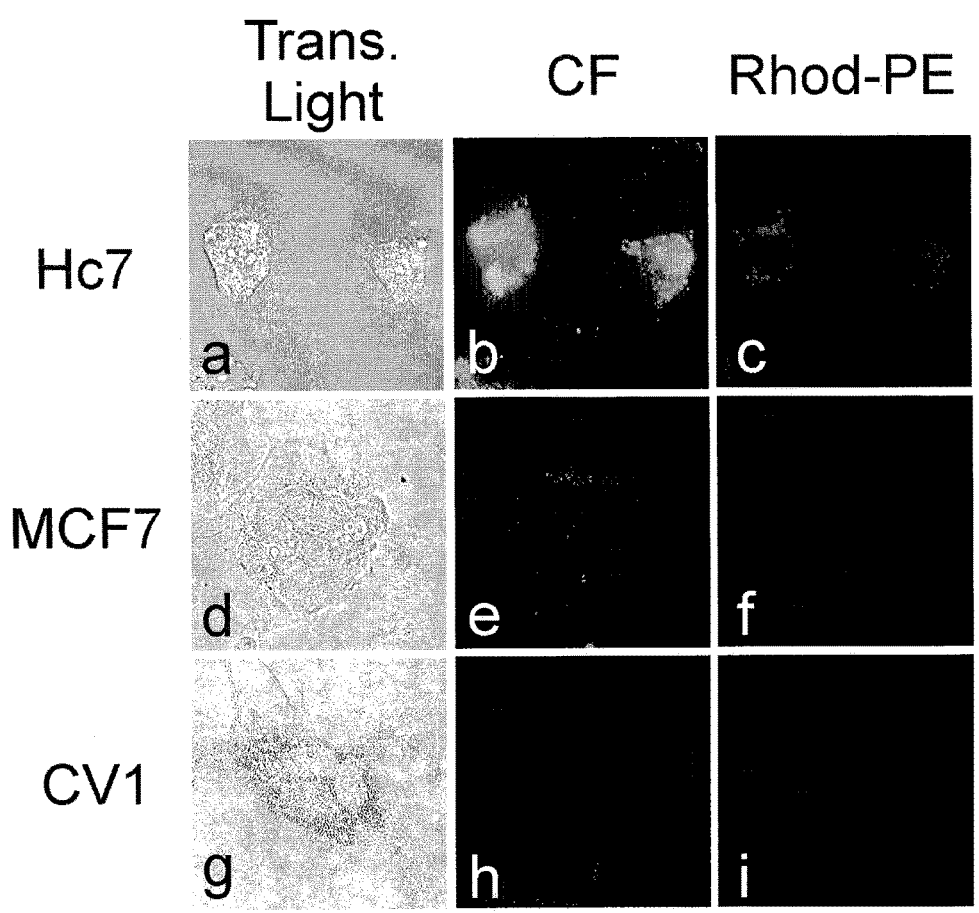

FIG. 13 shows that the incubation with anti-Her2 immunoliposomes containing Rhod-PE and encapsulating CF generates bright intracellular signals in Hc7 cells, but not MCF7 or CV1 cells. Panels a, d, and g are transmitted light images; panels b, e, and h show fluorescence in the fluorescein channel; panels c, f, and i show fluorescence in the rhodamine channel. HER2-overexpressing Hc7 cells (a-c) avidly endocytose immunoliposomes, resulting in de-quenching of CF to generate bright intracellular fluorescence. MCF7 cells (d-f) express a physiological level of HER2 and endocytose fewer liposomes, giving rise to only feeble fluorescence. CV1 cells (g-i), which express no HER2, exhibit no fluorescence.

Figure 14:
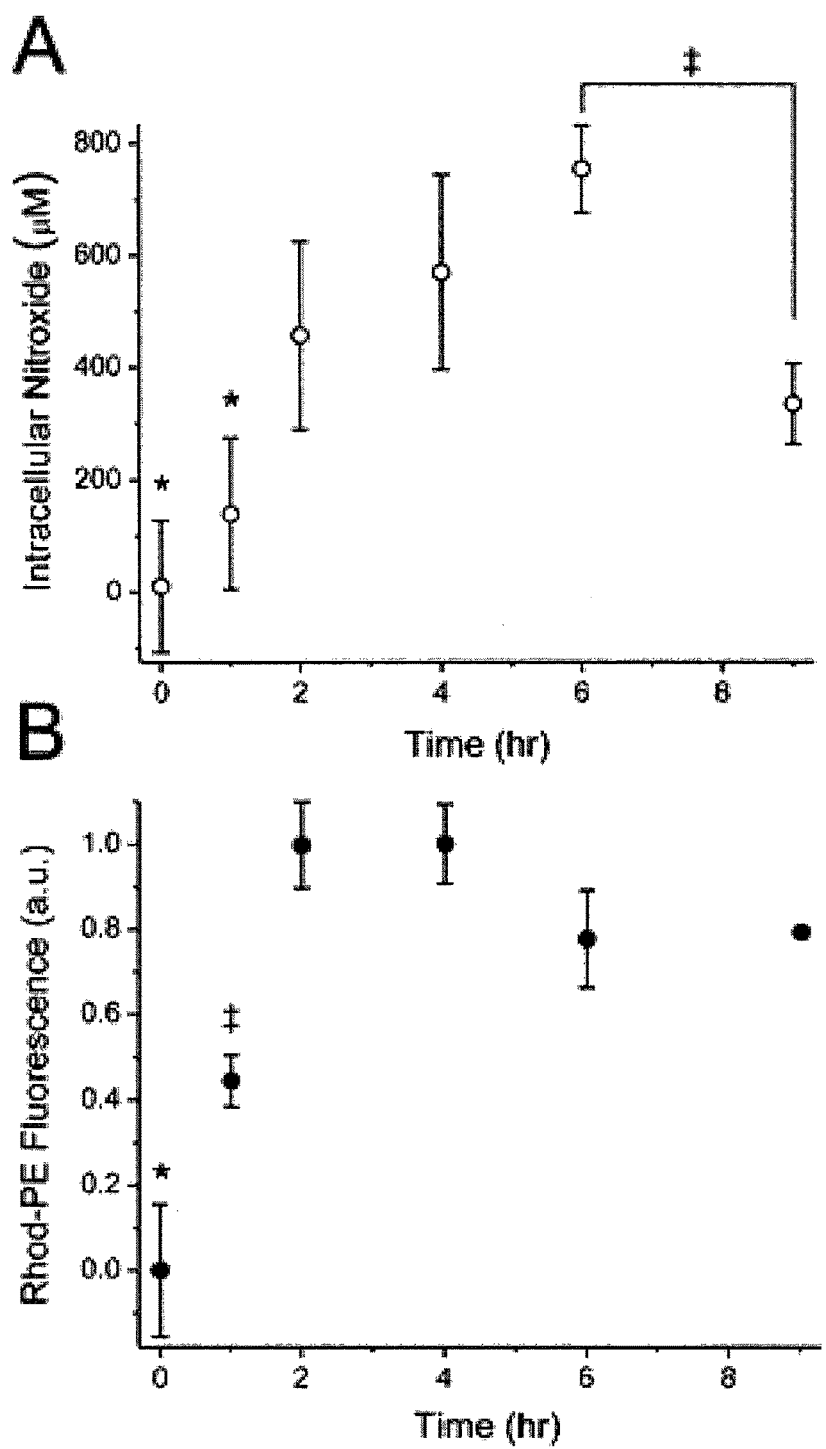

FIG. 14 shows the Hc7 cellular uptake of liposomes containing Rhod-PE (a fluorescent lipid tracer) and encapsulating nitroxide. Dishes of Hc7 cells were incubated at 37° C. with immunoliposomes containing Rhod-PE and loaded with nitroxide. At various times, intracellular nitroxide (A) and Rhod-PE (B) were assayed spectroscopically (n=3). After 6 hr, intracellular nitroxide increased to ~750 microM through immunoliposomal endocytosis as verified by parallel uptake of liposomal Rhod-PE. Beyond 6 hr, endocytosis slowed (evidenced by lack of further Rhod-PE accumulation) and intracellular nitroxide signal declined (error bars represent S.D.; where not seen, the bar was smaller than the symbol). Statistical significance (p<0.05) is denoted by asterisks and double-daggers. ANOVA values: panel A, $F_{5,17}=11.49$; panel B, $F_{5,17}=53.79$.

Figure 15:
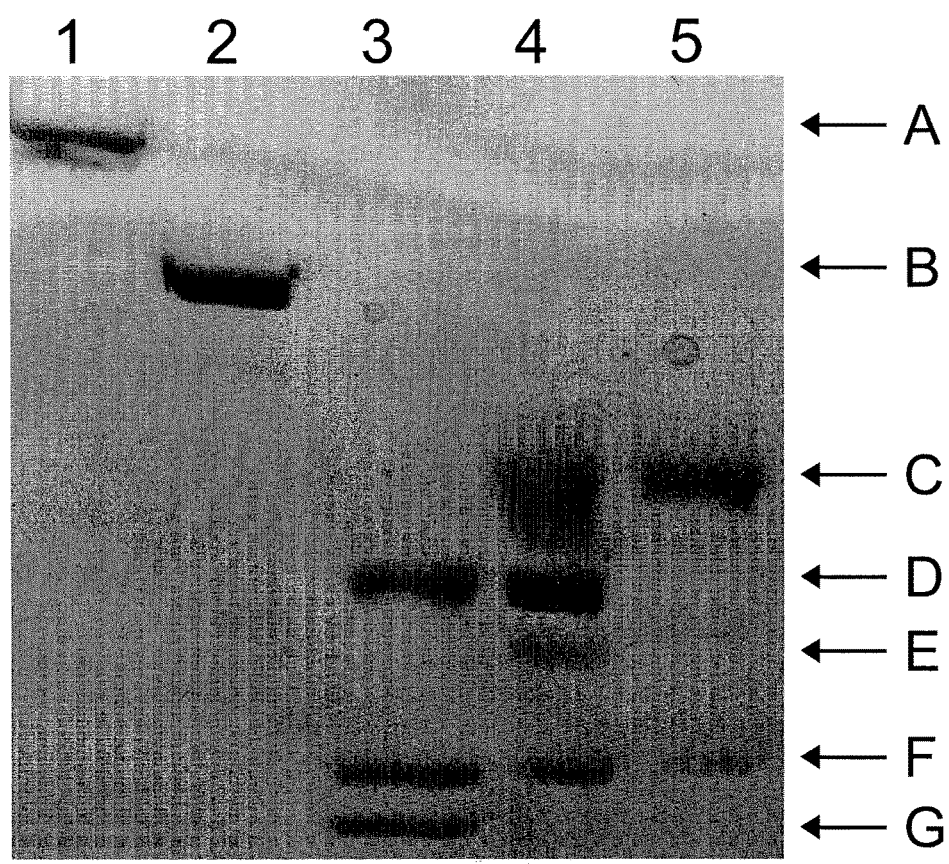

FIG. 15 shows the use of trastuzumab Fab' fragments and coupling to liposomes. Lane 1 is the whole antibody (band A) which was digested with pepsin to form F(ab')2 fragments (lane 2, band B). Reduction of F(ab')2 with cysteamine yielded Fab' fragments (lane 3, band D) with some reduction to non-immunoreactive heavy and light chains occurring (lane 3, bands F, G). Lane 4 shows an unpurified immunoliposome preparation. Fragments are attached to lipids bearing a 2000-kDa poly(ethyleneglycol) with a terminal maleimide. Linkage to the PEG-maleimide lipid increases the total molecular weight and causes a shift in fragment positions on the gel. Maleimide-coupled Fab' fragments (lane 4, band C) are distinct from those that were uncoupled (lane 4, band D). Additionally some coupling of individual heavy and light chains occurs (lane 4, bands E, F). Separation from uncoupled protein fragments is achieved by gel filtration and results in pure immunoliposomes that are predominantly labeled with trastuzumab Fab' fragments (lane 5).

Figure 16:
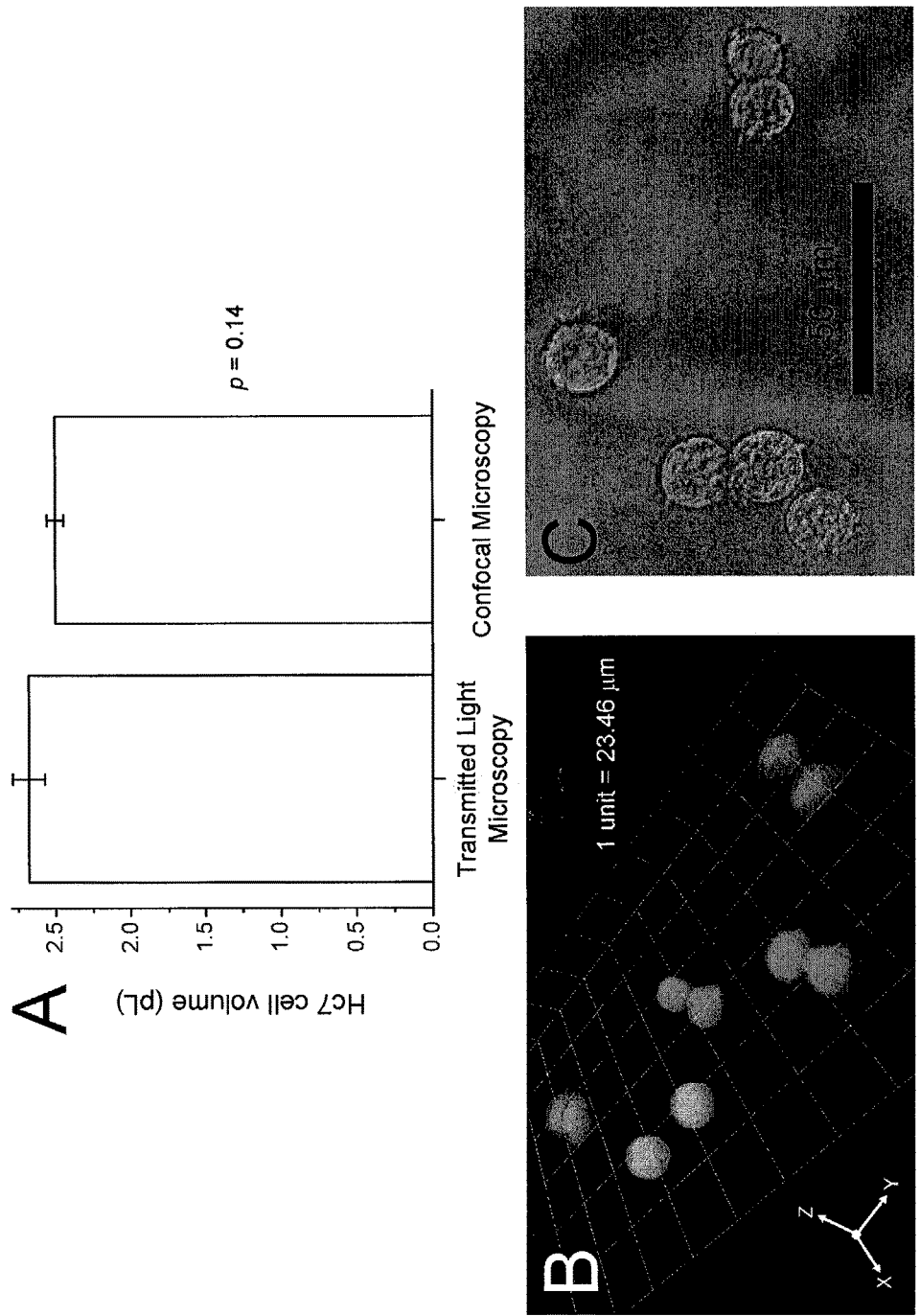

FIG. 16 shows the average Hc7 cell volume as determined independently by confocal and transmitted light microscopy.

Figure 17:
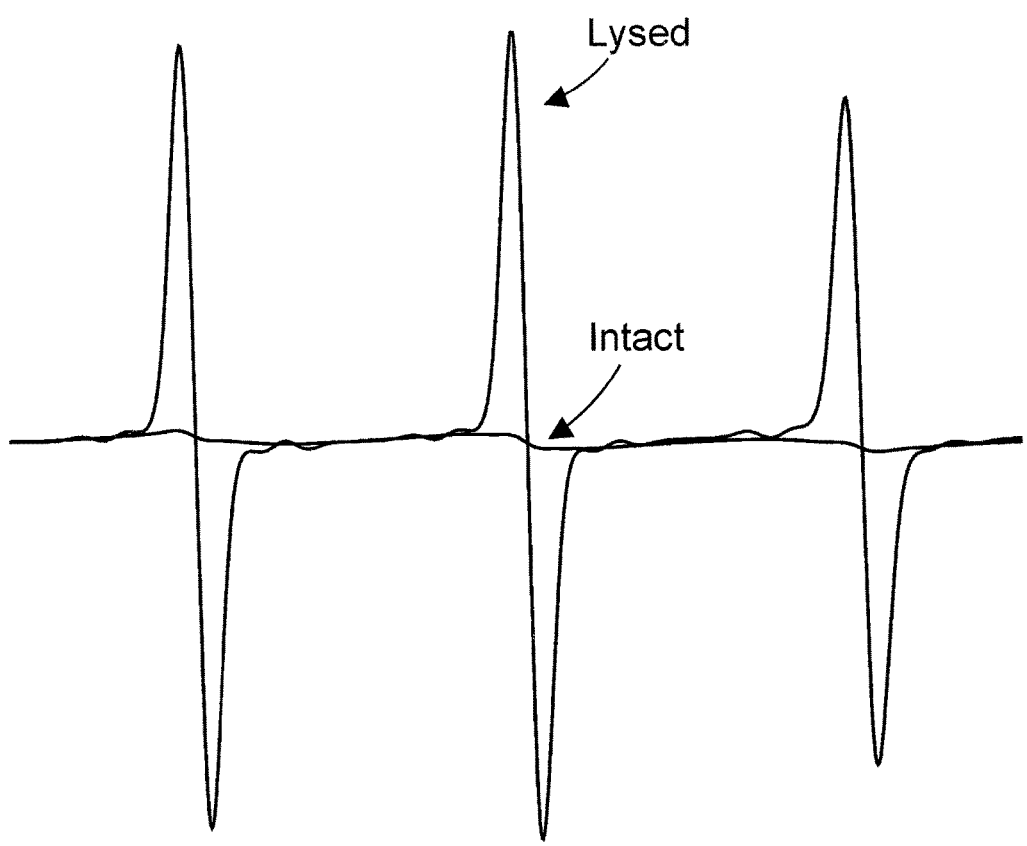

FIG. 17 shows that the immunoliposomes of the present invention can retain high concentrations of encapsulated nitroxides, such as between 50 and 300 mM of nitroxide, more preferably about 130 to 180 mM, and that exhibit a very weak signal due to quenching at a high concentration of nitroxides but once released into the bulk solution, the concentration is diluted and de-quenching occurs with an increased signal.

Figure 18:
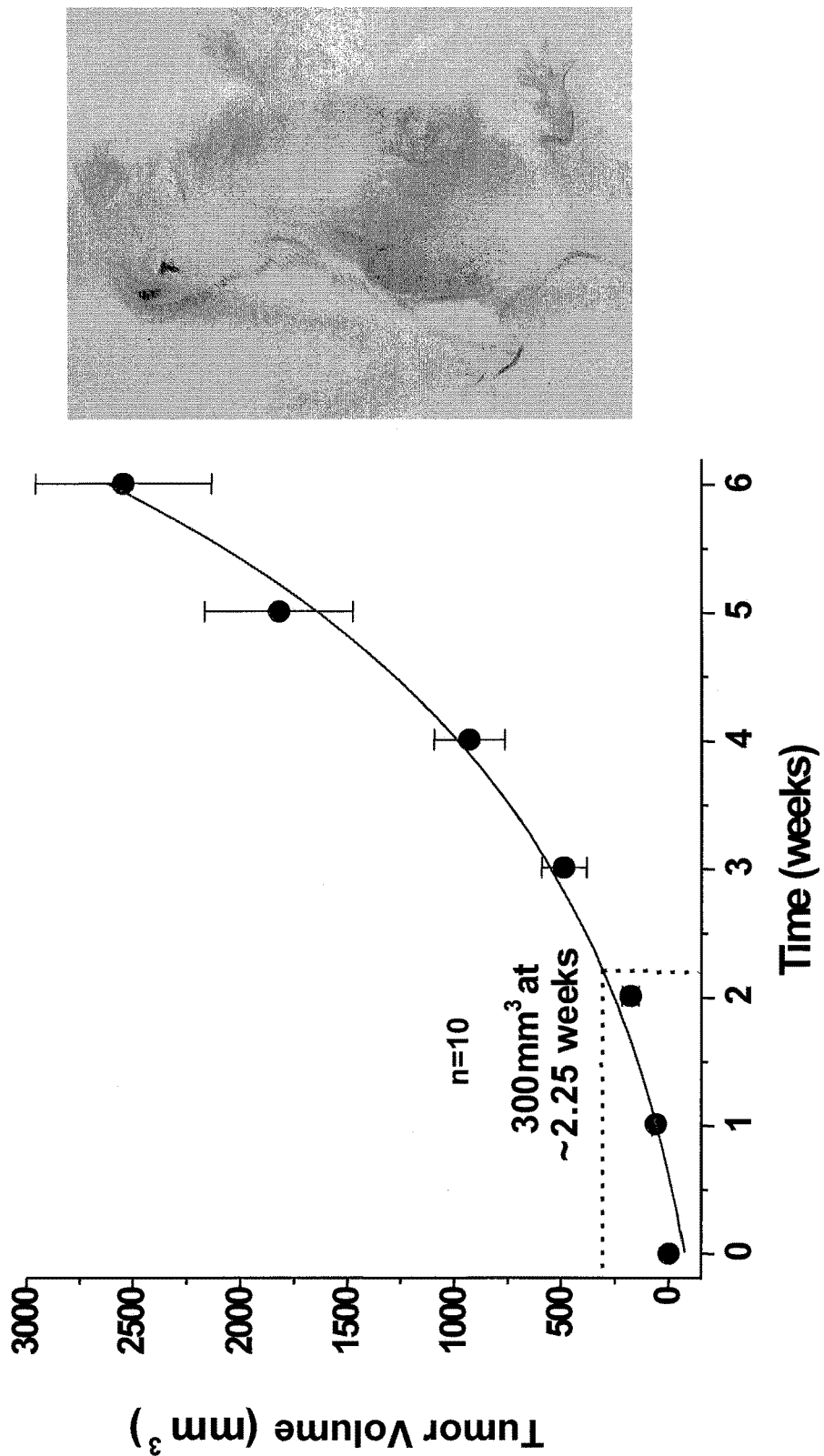

FIG. 18 shows growth of Hc7 xenograft tumors implanted in the flanks of SCID mice with an increase in volume of the tumor as the weeks progress, showing the Hc7 cells are a good in vivo model for HER2-overexpressing cancers.

Figure 19:
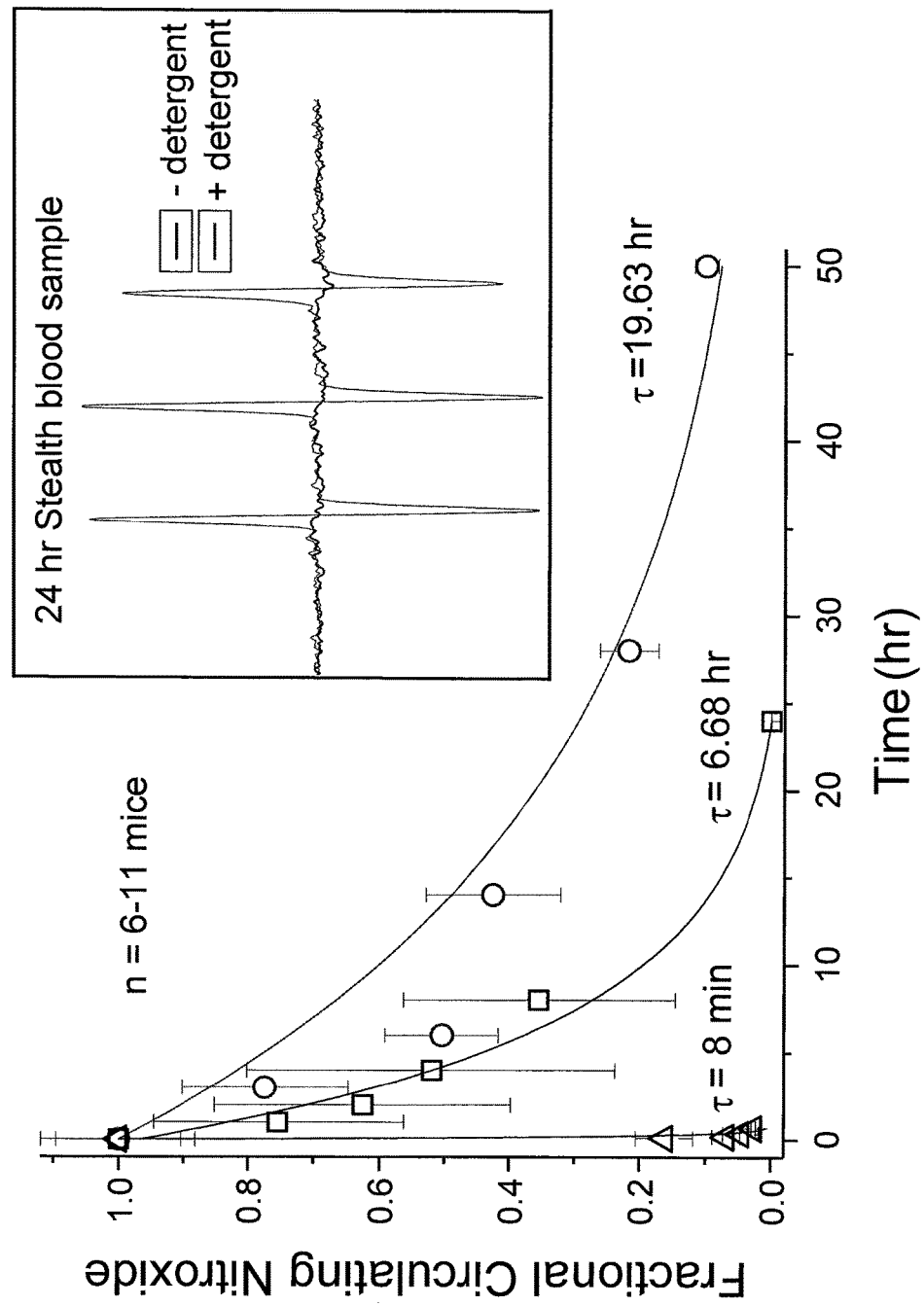

FIG. 19 shows the pharmacokinetics of nitroxide introduced into circulation in mice by different means: 1) injection of the nitroxide directly into circulation (triangles), 2) injection of nitroxide encapsulated in conventional liposomes bearing no poly(ethyleneglycol) on their surface (squares), and 3) injection of nitroxide encapsulated in "stealth" liposomes bearing poly(ethyleneglycol) on their surface (circles). The retention time (or lifetime, $\tau$) in circulation is most prolonged when nitroxides are encapsulated in "stealth" liposomes. The exponential life time ($\tau$) is related to the half-life ($t_{1/2}$): $t_{1/2}=0.693\tau$. Inset shows a blood sample drawn from a mouse 24 hours after receiving an injection of "stealth" liposomes encapsulating nitroxide. Without detergent lysis, the blood sample containing nitroxide-encapsulating liposomes gave essentially no spectral signal (thick black line). Upon addition of detergent, "stealth" liposomes in the blood were lysed to release their encapsulated nitroxide; the consequent de-quenching yielded a sharp three-peak spectrum with excellent signal-to-noise ratio (thin black line). The detergent lysis result shows that "stealth" liposomes encapsulating nitroxide are sufficiently structurally stable to retain nitroside at self-quenching concentrations even after 24 hours in circulation.

Figure 20:
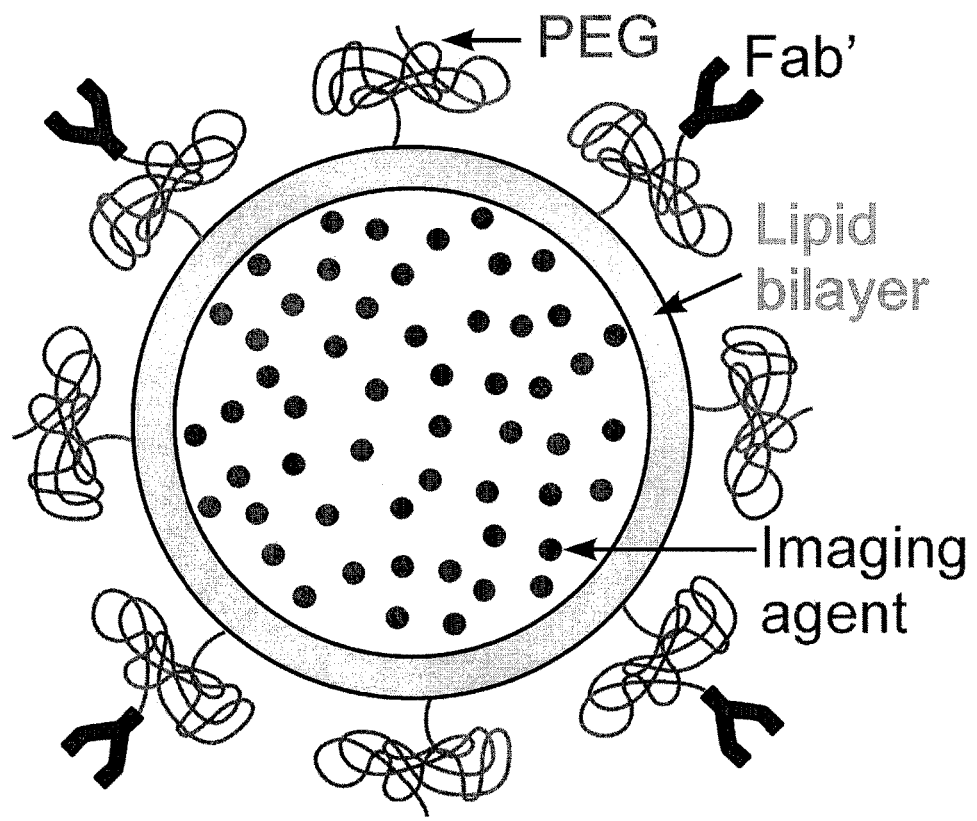

FIG. 20 illustrates a "stealth liposome" including nitroxide or trityl imaging agents and poly(ethyleneglycol) (PEG) moieties attached to the surface of the liposome and communicatively connected to a targeting ligand which in this case is a fragment of an antibody.

Figure 21:
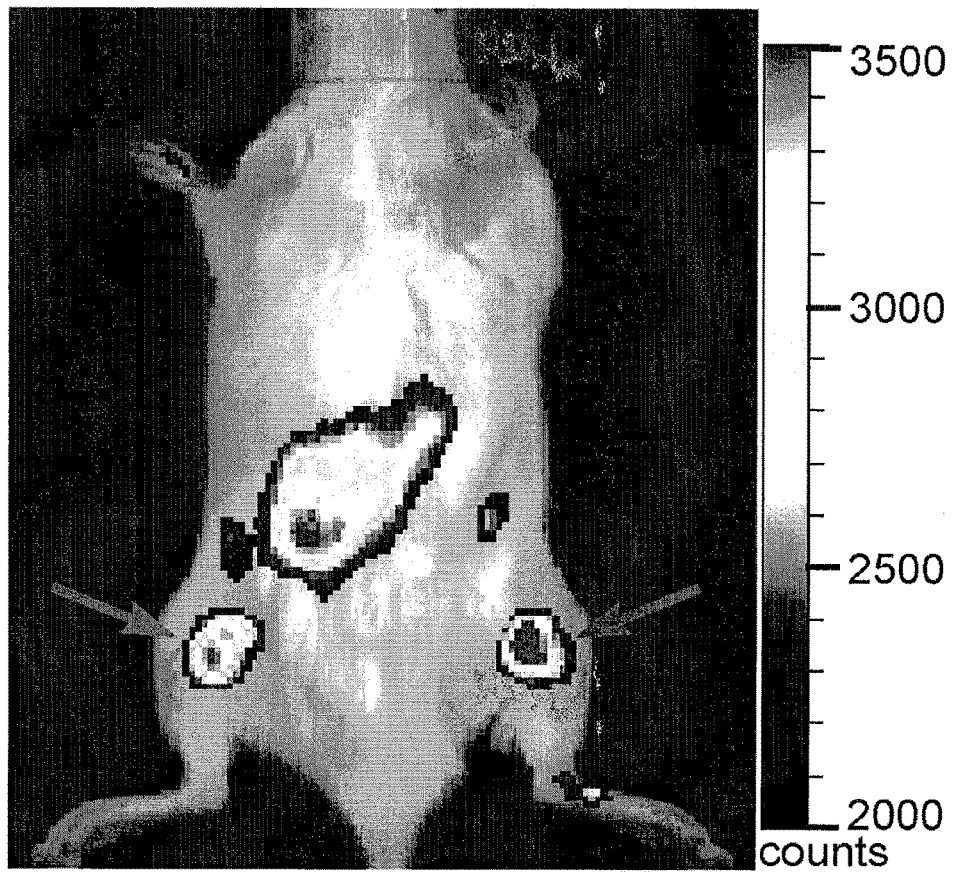

FIG. 21 shows uptake of "stealth immunoliposomes" by a tumor bearing mouse. The liposomes encapsulated the near-infrared fluorescent dye, indocyanine green (ICG), at self-quenching concentrations; therefore intact liposomes in circulation give no detectable fluorescence signal. Upon targeting to, and endocytosis by, the cells in the tumor. ICG is released from the liposomes into the cell. The consequent dilution and de-quenching results in bright ICG fluorescence.

Figure 22:
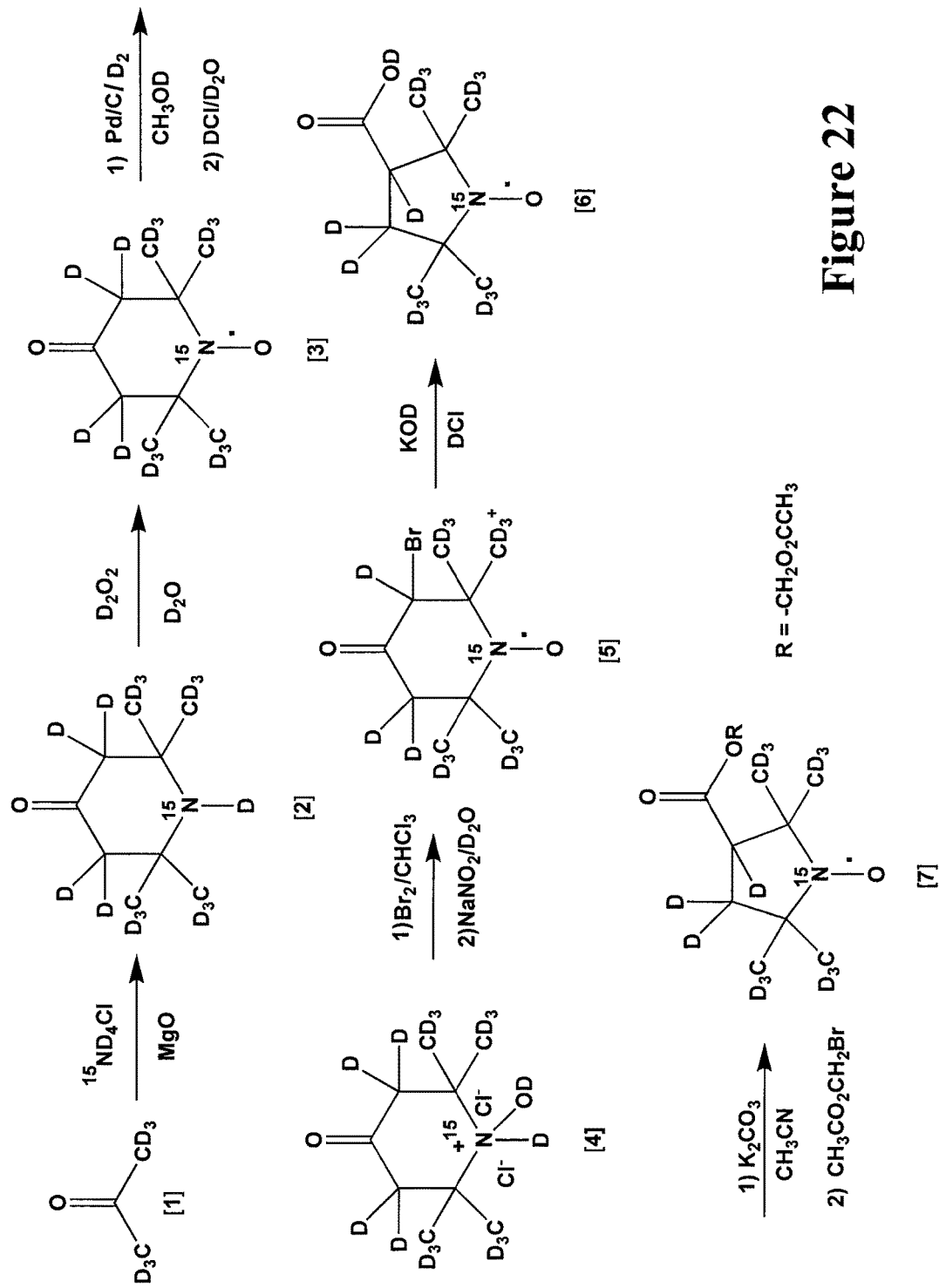

FIG. 22 shows a synthesis scheme for isotopic substitution of $^{15}N$ and $^{2}H$ in a pyrrolidinyloxyl ring.

Figure 23:
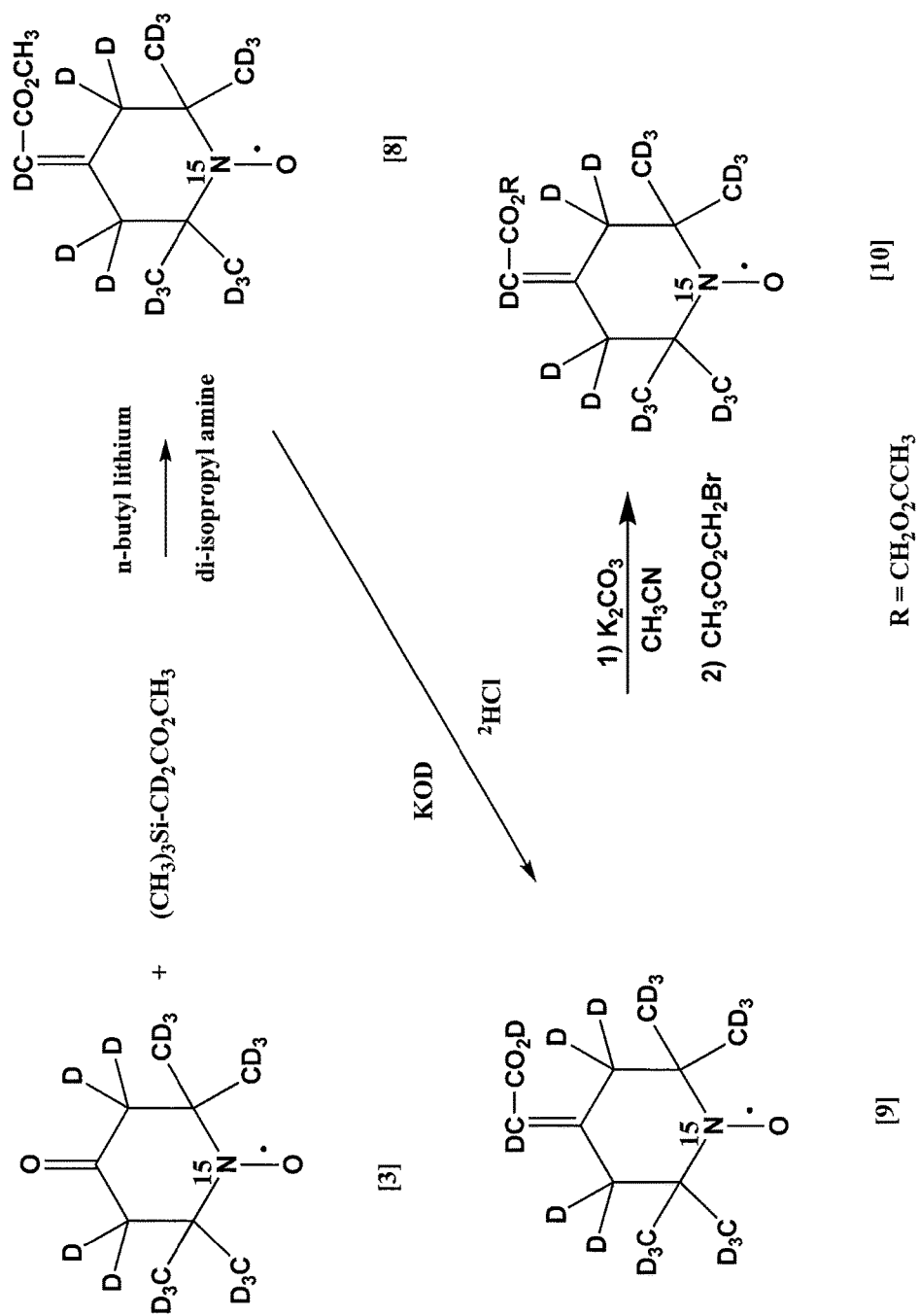

FIG. 23 shows a synthesis scheme for isotopic substitution of $^{15}N$ and $^{2}H$ in a piperidinyloxy ring.

DETAILED DESCRIPTION OF THE INVENTION

As used in the specification herein, "a" or "an" may mean one or more. As used herein in the claim(s), when used in conjunction with the word "comprising", the words "a" or "an" may mean one or more than one. As used herein "another" may mean at least a second or more.

"Tissue" as used herein refers to an individual cell or a plurality or aggregate of cells, for example, membranes, blood or organs. The term "tissue" also includes reference to an abnormal cell or a plurality of abnormal cells, such as cancerous cells. Exemplary tissues include myocardial tissue, including myocardial cells and cardiomyocites, membranous tissues, including endothelium and epithelium, laminae, connective tissue, including interstitial tissue, and tumors.

"Intracellular" or "intracellularly" as used herein refers to the area within the plasma membrane of a cell, including the protoplasm, cytoplasm and/or nucleoplasm, and/or the luminal space of intracellular organelles. "Intracellular delivery" refers to the delivery of photoactive agents, image contrast-enhancing agents, bioactive agents and/or targeting ligands into the area within the plasma membrane of a cell. "Cell" refers to any one of the minute protoplasmic masses which make up organized tissue, comprising a mass of protoplasm surrounded by a membrane, including nucleated and unnucleated cells and organelles. "Receptor" refers to a molecular structure within a cell or on the surface of a cell which is generally characterized by the selective binding of a specific substance. Exemplary receptors include cell-surface receptors for peptide hormones, growth factors, neurotransmitters, antigens, complement fragments, immunoglobulins and cytoplasmic receptors.

The term "antibodies," as used herein, means molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including but not limited to Fab fragment(s) and Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

The present invention provides for liposomes encapsulating nitroxides for delivery to targeted tissue and endocytosis and lysis within the cells for use as imaging agents in the tissue. Targeting such liposomes for specific cells or tissue can be accomplished by attaching a targeting ligand having affinity for the specific cells or tissue. Notably, detection can be accomplished without the use of ionizing radiation.

The movement of specific populations of cells through the body occurs in normal physiology as well as pathophysiology. Examples include the "homing" of lymphocytes to specific tissues and organs, and the spread of metastatic cancer cells from the original malignant lesion to distant sites. The ability to track and visualize such cell movements within the body would be useful clinically and scientifically. With the development of low-frequency electron paramagnetic resonance (EPR) spectroscopy and imaging, the ability to detect paramagnetic species in situ, in vivo and in real time, tracking and imaging of cells within a living animal is now a real possibility. In vivo concentrations of endogenous paramagnetic molecules are too low to be detected by EPR, and therefore it is necessary to use spin probes such as nitroxides to label and localize features of interest. However, to enable detection of the cells by low-frequency EPR spectroscopy, successful spin probes must be developed that are targeted to the specific cells, such as cancer cells. Further, the spin probes must be readily loaded into cells at high concentration and once loaded into cells, a spin probe must be well retained by the cells at physiological temperature in order to be useful for cell tracking studies in vivo.

The power of EPR spectroscopic techniques, using nitroxides, has several advantages over other imaging modalities. First, the radiofrequency waves used to excite resonance penetrates tissues well, enabling imaging of deep tissues with high signal-to-noise ratios (SNR) and high spatial resolution. Second, spin probes such as nitroxides or trityl radicals can be designed to be sensitive to cellular physiology; therefore, in addition to localizing a tumor, they can also report on its physiology. Physiological parameters that can be measured with spin probes include tissue oxygen tension (Elas et al, 2006; Shen, et al., 2006; Elas et al, 2008), microviscosity—a measure of how easily small molecules can diffuse locally (Halpern et al, 1999), pH (Khramtsov et al, 1982), temperature (Dreher et al, 2004), and redox status (Utsumi et al, 2006).

Nitroxides were previously synthesized that exhibit long-lived intracellular signals and are imagable by EPR. (Kao et al, 2007; Rosen et al, 2005). Notably the synthesized nitroxides, like fluorophores, when encapsulated in liposomes at very high concentrations (>100 mM), exhibit concentration-dependent signal quenching. Thus, intact liposomes containing quenched probes are spectroscopically undetectable. After endocytosis, lysis of the liposomes liberates the encapsulated probes into the cell, the resulting dilution de-quenches the probe signal to make the cell visible (Burks et al, 2009). Encapsulation of probes at high concentrations minimizes background signal from unendocytosed liposomes and creates a cell-activated signal-generating mechanism thereby allowing sufficient intracellular accumulation of nitroxides to permit EPR imaging. However, heretofore targeting the liposome-based contrast-generating system to specific tissue was not available.

In order to deliver EPR imaging agents to a physiologically distinct tissue, liposomes must be made targetable, that is, they must incorporate some feature that induces selective uptake in a tissue of interest, but not in other, indifferent, tissues. Liposomal surfaces are readily decorated with moieties that make them targetable to a particular tissue. Anti-HER2 immunoliposomes have monoclonal antibody fragments against HER2 attached to their surfaces which are used to enhance selective delivery of drugs like doxorubicin (Mamot et al, 2003; Park et al, 2002; Park et al, 2001). Immunoliposomes are an attractive alternative to the above-mentioned delivery approaches in which "cargo" molecules are conjugated directly to the antibody. Those approaches typically deliver only a few molecules per antibody, and are therefore not efficient for imaging applications, where large numbers of probe molecules must be delivered to maximize imagable signal. Immunoliposomes encapsulating high concentrations of probe molecules, such as between 100 mM and 300 mM, have the advantage that they can greatly improve intracellular signal amplification for imaging probes.

In one embodiment of the present invention provides for inclusion of stable free-radicals nitroxides or trityl radicals in a liposome, including but not limited to the nitroxide structures shown below.

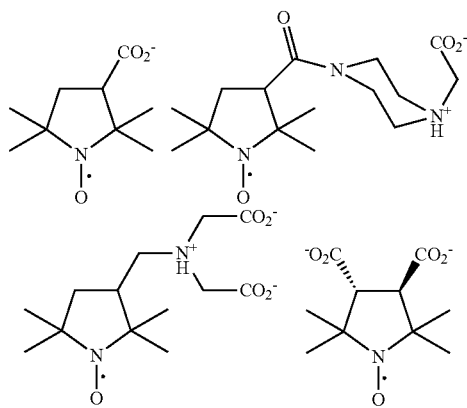

Notably, the longer the nitroxide molecules stay in the cells, the wider the temporal window during which EPR spectroscopic measurements can be obtained. FIG. 1 shows preferred nitroxides of the present invention and FIG. 7 shows the intracellular retention of such nitroxide probes. It is evident that nitroxide [3] has a significant increase in retention time and approximately a 4-fold improvement over nitroxide [2] and a 12 fold increase over nitroxide [1].

The present invention is useful in delivering the detection probes to specific tissues of interest. The use of liposomes encapsulating the detection probes facilitates this delivery. Liposomes are particles formed from the assembly of amphiphilic lipid molecules to form a bilayer structure with a generally spherical or spheroidal geometry, and the structure may be in the form of one or more concentric laminae (i.e., unilamellar or multilamellar). The two polar surfaces of each bilayer face an internal aqueous compartment and an external aqueous compartment, respectively. Liposomes may also be referred to as lipid vesicles or lipid microspheres. The liposomes may be formulated, for example, from ionic lipids and/or non-ionic lipids.

The size of the liposomes of the present invention will depend upon the intended use. Sizing also serves to modulate resultant liposomal biodistribution and clearance, which can be determined by one skilled in the art. In addition to filtration, the size of the liposomes can be adjusted, if desired, by procedures known to one skilled in the art, such as shaking, microemulsification, vortexing, filtration, repeated freezing and thawing cycles, extrusion, extrusion under pressure through pores of a defined size, sonication, homogenization, the use of a laminar stream of a core of liquid introduced into an immiscible sheath of liquid. Extrusion under pressure through pores of defined size is a preferred method of adjusting the size of the liposomes.

Since liposome size influences biodistribution, different size liposomes may be selected for various purposes. For example, for intravascular application, the preferred size range is a mean outside diameter between about 30 nm and about 10 micromolar. To provide therapeutic delivery to organs such as the liver and to allow differentiation of tumor from normal tissue, smaller vesicles, between about 30 nm and about 200 nm in mean outside diameter, are preferred. For intranasal, intrarectal or topical administration, the vesicles are preferably less than about 100 micromolar in mean outside diameter. Large vesicles, between 1 and about 10 micromolar in size, will generally be confined to the intravascular space until they are cleared by phagocytic elements lining the vessels, such as the macrophages and Kupffer cells lining capillary sinusoids. For passage to the cells beyond the sinusoids, smaller vesicles, for example, less than about 300 nm in size, may be utilized. For in vitro assay use, such as cell culture applications, the liposomes may be added to the cells in cultures and then incubated. For pulmonary applications, dried or lyophilized powdered compositions may be administered via inhaler. Aqueous suspensions of liposomes may be administered via nebulization. Further, the imaging probe liposomes may be administered in the form of an aqueous suspension such as in water or a saline solution (e.g., phosphate buffered saline). The solution may be buffered, if desired, to provide a pH range of about 5 to about 8.

A wide variety of lipids may be used as stabilizing materials and vesicles in the present invention. The lipids may be of natural, synthetic or semi-synthetic origin, including for example, fatty acids, neutral fats, phosphatides, oils, fluorinated oils, glycolipids, surface active agents, aliphatic alcohols, waxes, terpenes and steroids. Suitable lipids which may be used to prepare the stabilizing materials of the present invention include, for example, fatty acids, lysolipids, fluorinated lipids, phosphocholines; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids; glucolipids; sulfatides; glycosphingolipids; phosphatidic acids, such as dipalmitoylphosphatidic acid (DPPA) and distearoyl-phosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxy-alkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN®, including, for example, TWEEN® 20, TWEEN®0.40 and TWEEN® 80), glyceryl polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; and/or any combinations thereof. Several acceptable methods for forming liposomes are known in the art.

Figure 2:
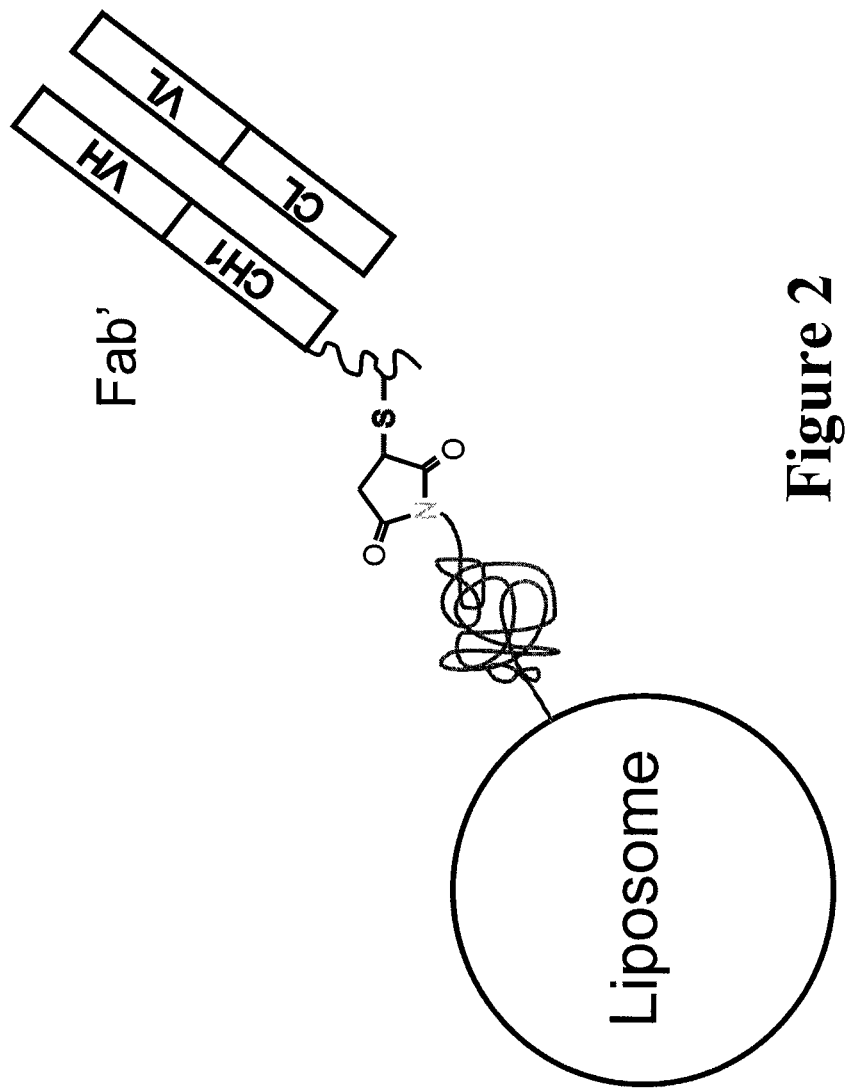
FIGS. 2 and 3 show alternative linking groups including antibody fragments for attachment to the liposome.
Figure 3:
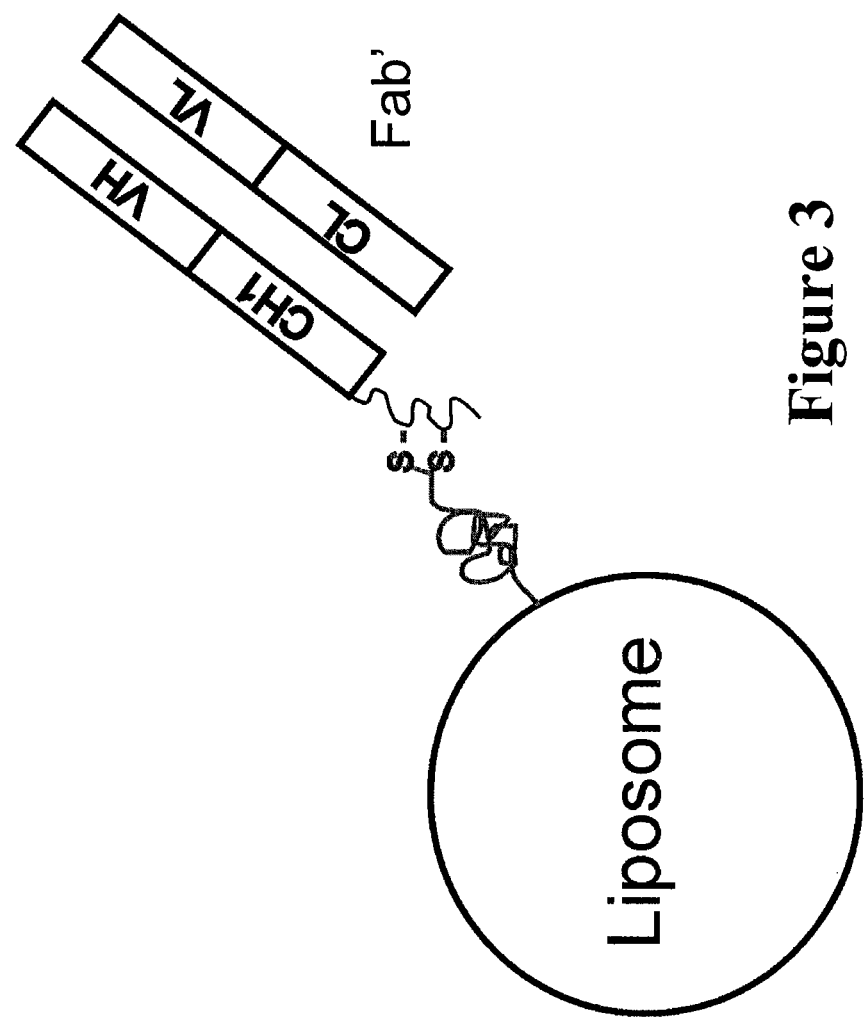

The liposomes of the present invention include a targeting ligand positioned on its surface for targeting of tissues and/or receptors both in vivo and/or in vitro. The targeting ligand may be synthetic, semi-synthetic, or naturally-occurring. Materials or substances which may serve as targeting ligands include, for example, proteins, including antibodies, antibody fragments, monoclonal antibodies, hormones, hormone analogues, glycoproteins and lectins, peptides, polypeptides, amino acids, sugars, saccharides, including monosaccharides and polysaccharides, carbohydrates, vitamins, steroids, steroid analogs, and genetic material, including nucleosides, nucleotides, nucleotide acid constructs and polynucleotides. FIGS. 2, 3 and 20 show examples of linkers and antibody fragments attached to a liposome.

Antibodies that may be modified according to the present invention include, but are not limited to cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, 1-131 tositumomab, efalizumab, bevacizumab, panitumumab, pertuzumab, natalizumab, etanercept, IGN101 (Aphton), volociximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), eraptuzumab (Immunomedics), MDX-010 (Medarex and BMS), MDX-060 (Medarex), MDX-070 (Medarex), matuzumab (Merck), CP-675,206 (Pfizer), CAL (Roche), SGN-30 (Seattle Genetics), zanolimumab (Serono and Genmab), adecatumumab (Sereno), oregovomab (United Therapeutics), nimotuzumab (YM Bioscience), ABT-874 (Abbott Laboratories), denosumab (Amgen), AM 108 (Amgen), AMG 714 (Amgen), fontolizumab (Biogen Idec and PDL BioPharm), daclizumab (Biogent Idec and PDL BioPharm), golimumab (Centocor and Schering-Plough), CNTO 1275 (Centocor), ocrelizumab (Genetech and Roche), HuMax-CD20 (Genmab), belimumab (HGS and GSK), epratuzumab (Immunomedics), MLN1202 (Millennium Pharmaceuticals), visilizumab (PDL BioPharm), tocilizumab (Roche), ocrerlizumab (Roche), certolizumab pegol (UCB, formerly Celltech), eculizumab (Alexion Pharmaceuticals), pexelizumab (Alexion Pharmaceuticals and Procter & Gamble), abciximab (Centocor), ranibizimumab (Genetech), mepolizumab (GSK), TNX-355 (Tanox), or MYO-029 (Wyeth).

The targeting ligand can be attached to the liposome using any technique available to the skilled artisan. Such techniques include, but are not limited to, ionic bonds, covalent bonds, hydrogen bonds, and combinations thereof. The targeting ligand is preferably covalently bound to the surface of the liposome by a spacer including, for example, hydrophilic polymers, such as the hydrophilic polymers described herein, preferably polyethylene glycol. FIG. 20 is representative of an immunoliposome of the present invention wherein PEG molecules are used as linkers between the targeting ligand and the surface of the liposome.

Exemplary covalent bonds by which the targeting ligands are associated with the stabilizing materials include, for example, maleimide; amide (—CONH—); thioamide (—CSNH—); ether (ROR'), where R and R' may be the same or different and are other than hydrogen); thioether (RSR'), ester (—COO—); thioester (—COS—); —O—; —S—; —Sn—, where n is greater than 1, preferably about 2 to about 8, and more preferably about 2; carbamates; —NH—; —NR—, where R is alkyl, for example, alkyl of from 1 to about 4 carbons; and substituted imidate; and combinations of two or more of these.

Covalent bonds between targeting ligands and, for example, lipids used for the liposome, may be achieved through the use of molecules that may act as spacers to increase the conformational and topographical flexibility of the ligand. Such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like. In addition, in the case of targeting ligands which comprise peptide moieties, side chain-to-side chain crosslinking may be complemented with side chain-to-end crosslinking and/or end-to-end crosslinking. Also, small spacer molecules, such as dimethylsuberimidate, may be used to accomplish similar objectives.

Targeting ligands may be selected for targeting specific antigens on the tissue of interest, including antigens associated with breast cancer, such as epidermal growth factor receptor (EGFR), fibroblast growth factor receptor, erbB2/HER-2 and tumor associated carbohydrate antigens. CTA 16.88, homologous to cytokeratins 8, 18 and 19, is expressed by most epithelial-derived tumors, including carcinomas of the colon, pancreas, breast, ovary and lung. Thus, antibodies directed to these cytokeratins, such as 16.88 (1 µM) and 88BV59 (IgG3k), which recognize different epitopes on CTA 16.88 may be employed as targeting ligands. For targeting colon cancer, anti-CEA IgG Fab' fragments may be employed as targeting ligands. Chemically conjugated bispecific anti-cell surface antigen, anti-hapten Fab'-Fab antibodies may also be used as targeting ligands. The MG series monoclonal antibodies may be selected for targeting, for example, gastric cancer.

Detection of paramagnetic probes may be accomplished by using electron paramagnetic resonance (EPR) spectroscopy which is a technique for observing the behavior of free radicals by detecting changes in the energy state of unpaired electrons in the presence of a magnetic field. The technique is specific for free radicals because only unpaired electrons are detected. Using electron paramagnetic resonance (EPR) spectrometer, a real-time image of a macroscopic object, including living tissue can be obtained. EPR imaging (ERI) provides the capability to obtain multi-dimensional images (including spectral-spatial images) for diagnosis or research.

Under most circumstances, free radical reactions occur so rapidly and free radicals are so short-lived that EPR imaging can be difficult. However, due to the presence of the stable free radicals, such as the nitroxides described herein, the presently claimed nitroxides are detectable by electron paramagnetic resonance spectroscopy. With the development of advanced low-frequency EPR spectrometers, images of intact biological tissues and organs are available based on a measurement of free radical concentration. Pursuant to this invention, nitroxide levels in the body may be maintained for a prolonged period of time allowing both improved image contrast and longer signal persistence.

Notably, significant improvements in signal to noise ratio (SNR) are possible through rational refinement of the nitroxide molecular structure. Hyperfine interactions at the nitrogen ($^{14}N$) atom cause an otherwise sharp, single resonance to split into three broader peaks, each having one-third the total intensity. In imaging, the height of only a single peak is measured. Therefore, SNR can be improved by preparing nitroxides containing $^{15}N$, which gives rise to two spectral lines, each with half of the total intensity as shown in FIG. 9. The result is a 50% increase in the single-peak signal. Hyperfine splitting due to hydrogen atoms broadens each peak in the nitroxide spectrum. The broader peak means resonance occurs over a greater range of magnetic field. This translates into reduced spatial resolution as magnetic field gradients are used for spatial imaging. Because deuterium atoms have much weaker hyperfine interactions than hydrogen atoms, perdeuteration of the nitroxide will sharpen the EPR spectral peaks significantly. In consequence, perdeuteration improves spatial resolution as well as SNR, as shown in FIG. 9, wherein the width of the signal is narrowed but the intensity is greatly increased.

The present invention provides evidence that immunoliposomes, having a concentrated level of nitroxides, can be synthesized, delivered to a cell and incorporated therein to provide a detectable signal.

Further, the examples discussed herein below demonstrate that immunoliposomes bearing trastuzumab Fab' fragments having high targeting specificity for Hc7 cells and incorporated within such cells. A stable HER2-overexpressing cell line was generated, that being Hc7, which is derived from the MCF7 human breast tumor line. The developed Hc7 cells express high levels of HER2 at the plasma membrane, making them an ideal target for immunoliposomal targeting. Notably, immunoliposomes encapsulating quenched fluorophores generate intense fluorescence signals after endocytosis by Hc7 cells, but not by cells that do not express, or express only physiological levels of, HER2. Furthermore, Hc7 cells endocytose nitroxide-loaded immunoliposomes and accumulate intracellular nitroxide concentrations sufficient to enable EPRI with high contrast in vivo. Thus the present invention shows that EPRI and nitroxides can be used for visualization and investigation of HER2-overexpressing tumors in animals.

EXAMPLES

General Materials and Methods

The nitroxide (2,2,5,5-tetramethylpyrrolidin-1-oxyl-3-yl-methyl)amine-N,N-diacetic acid was synthesized as described previously (Rosen et al, 2005). 6-Carboxyfluorescein (CF) was from Sigma (St. Louis, Mo.). The nitroxide and CF free acids were converted to the corresponding potassium salts by addition of stoichiometric equivalents of KOH. Lipids were from Avanti Polar Lipids (Alabaster, Ala.), and cell culture media and biochemicals were from Invitrogen (Carlsbad, Calif.), Life Technologies (Grand Island, N.Y.), or Sigma. All chromatography resins were from Pharmacia Fine Chemicals (Piscataway, N.J.), or GE Healthcare (Piscataway, N.J.). UV-visible spectroscopy was used to quantify total protein and free sulfhydryl groups. Samples were read on Wallac Victor2 1420 multilabel count plate reader (Perkin-Elmer, Waltham, Mass.). Protein content was measured by absorbance at 595 nm after 5 µL of sample was diluted into 250 µL of premixed Coomassie Brilliant Blue G-250 solution (Sigma). Free sulfhydryl groups were determined by absorbance at 412 nm in the presence of 0.004% w/v 5,5'-dithio-bis-(2-nitrobenzoic acid). Data analyses and presentation were performed with Origin 8.0 (OriginLabs, Northampton, Mass.), Adobe Photoshop CS3 (Adobe Corp., San Jose, Calif.), and Velocity 5.1 (Improvision, Waltham, Mass.).

Statistical Analysis

The Student's t-test at a 95% confidence interval (p<0.05) was used to determine significance between data sets containing only two groups. One-way ANOVA analysis was used to determine differences among data sets containing more than two groups. A 95% confidence interval (p<0.05) was used to determine significance, and post-hoc analysis was performed according to the Bonferroni method of means comparison.

Cell Culture

CV1 (American Type Culture Collection, Manassas, Va.) and MCF7 cells were maintained at 37° C. under 5% CO2 atmosphere, in Dulbecco's Modified Eagle Medium (DMEM) supplemented with 10% fetal bovine serum (FBS), 2 mM L-glutamine, 100 U/mL penicillin, and 100 µg/mL streptomycin (Pen/Strep). Hc7 cells were cultured under the same conditions except the medium also contained 500 µg/mL hygromycin B.

Transfection of MCF7 Cells with HER2 cDNA

A pcDNA3.1 vector incorporating HER2 cDNA and a hygromycin selection marker (gift from Dr. Anne Hamburger, University of Maryland Baltimore) was stably transfected into MCF7 cells. Fugene-6 (10% v/v) (Roche Molecular Biochemicals, Indianapolis, Ind.) was incubated at room temperature for 5 minutes in FBS-free, antibiotic-free DMEM. Plasmid DNA was added (39 µg/mL) and incubated for 30 min at room temperature. 100 µL of plasmid/transfection reagent complex was added to 8 mL FBS-containing, antibiotic-free DMEM and used to transfect 2×105 MCF7 cells plated on 60-mm plastic Petri dishes. After 24 hr, the transfection medium was replaced with fresh DMEM containing FBS and Pen/Strep. Hygromycin B (500 µg/mL) was added to the medium 96 hr after transfection. Antibiotic-resistant colonies were isolated and passed >10 times prior to analysis for HER2 overexpression.

Western Immunoblotting

Hc7 cells were lysed in radio-immunoprecipitation assay (RIPA) buffer. 50 µg of total protein was resolved by SDS-PAGE under reducing conditions. Proteins were transferred to Hybond-ECL nitrocellulose membranes (Biorad, Hercules, Calif.) and probed with rabbit-anti-human antibodies against phospho-HER2 and β-actin (Millipore, Billerica, Mass.). A secondary hybridization was done with horse-radish-peroxidase (HRP) conjugated, anti-rabbit antibodies, and visualization used an enhanced chemiluminescence (ECL) detection kit (Biorad). All antibodies were used at concentrations recommended by the suppliers.

Preparation of Trastuzumab Fab' Fragments for Immunoliposomes

Trastuzumab (8 mg/mL) in 20 mM sodium acetate (final pH 4.5) was added to 125 µL of immobilized pepsin gel (Pierce Biotechnology, Rockford, Ill.) which had been washed three times in acetate buffer. Pepsin digestion for 4 hr at 37° C. yielded F(ab')2 fragments. The reaction was stopped by the addition of 1M Tris solution until final pH was 6.5. The pepsin gel was removed by centrifugation.

The F(ab')2 fragments were converted to Fab' fragments by reduction with 50 mM cysteamine at 37° C. for 45 min. The reaction mixture was chromatographed on a Sephadex G-15 column equilibrated with the following buffer: 100 mM sodium chloride, 50 mM sodium citrate, 2 mM disodium ethylenediamine tetraacetic acid (EDTA), pH 6.7, and purged with N2 (type NF, Airgas East Inc., Salem, N.H.) for 30 min. Fractions containing Fab' fragments were collected under N2 atmosphere, immediately frozen in liquid N2, and maintained at −80° C. until use.

Preparation of Trastuzumab Fab' Fragments for Immunostaining

For experiments involving Fab' fragments not coupled to liposomes, it is necessary to prevent reformation of (Fab')2 fragments under aerobic conditions. Fab' fragments were prepared as outlined above, and then free sulfhydryl groups were inactivated by addition of 20 mM maleimide at 4° C. for 8 hr under N2 atmosphere. After the reaction was complete, the inactivated fragments were separated from unreacted maleimide on a Sephadex G-15 column with Dulbecco's Phosphate Buffered Saline (DPBS) as eluent.

HER2 Immunostaining

MCF7 and Hc7 cells were cultured on 25-mm No. 1 glass coverslips for 24-48 hr. All steps in the staining procedure were at room temperature; following each step, cells were washed three times with DPBS. Cells were fixed with 4% paraformaldehyde in DPBS (final pH 7.4) for 20 min. Blocking of non-specific antigen sites was done with 10% normal rabbit serum in DPBS for 1 hr. Primary antibodies in DPBS were incubated with cells for 3 hr. Concentrations of the primary antibodies used were: trastuzumab, 1 µg/mL; maleimide-inactivated trastuzumab Fab', 0.38 µg/mL. The secondary antibody was a fluorescein isothiocyanate (FITC)-conjugated, Fab-specific, rabbit anti-human IgG (Jackson Immuno, West Grove, Pa.), and was used at 3 µg/mL in DPBS. Secondary antibody hybridization was done for 1 hr with samples protected from light. Cells were then maintained in fresh DPBS and FITC fluorescence was imaged by fluorescence microscopy.

Immunoliposome Preparation

Liposomes were composed of 1,2-distearoyl-phosphatidylcholine (DSPC), cholesterol (Chol), 1,2-dipalmitoyl-phosphatidylethanolamine-N-(lissamine rhodamine B sulfonyl) ammonium salt (Rhod-PE), and 1,2-distearoyl-sn-glycero-3-phosphoethanolamine-N-[maleimide (polyethyleneglycol)2000] ammonium salt (PE-PEG-maleimide) in the molar ratio 3 DSPC:2 Chol:0.06 PE-PEG-maleimide:0.003 Rhod-PE. A solution of 10-30 mmoles phospholipid in 100 µL EtOH was injected into 0.5 mL of a rapidly-stirred aqueous solution of 100 mM CF or 150 mM nitroxide. The mixture was extruded 11 times through a 100-nm porosity filter membrane in a Mini Extruder (Avanti Polar Lipids) to yield a suspension of liposomes. All solutions and the extruder were maintained at a temperature >55° C. to ensure fluidity of the lipid phase. The liposomes were purified on a Sephadex G-50 column in the same anaerobic buffer used to purify Fab' fragments. Trastuzumab Fab' fragments, prepared as outlined above, were incubated with freshly-prepared liposomes under N2 atmosphere at 4° C. overnight. Resulting immunoliposomes were purified on Sephacryl HR-200 with DPBS as eluent and were stored at 4° C. until use.

Samples containing 20 µg total protein were resolved by SDS-PAGE under non-reducing conditions and stained with Coomassie Brilliant Blue according to standard protocols. Antibody coupling was verified by SDS-PAGE (FIG. 15). Purified immunoliposomes encapsulating the 150 mM nitroxide were measured by EPR spectroscopy before and after lysis. Intact liposomes (linear trace) retain enough nitroxide through the antibody coupling procedure to exhibit quenched signal. Lysis was achieved with the addition of 1% v/v Triton X-100, and sonication for 1 min. Lysed liposomes (peaks) exhibit de-quenched signal that is ~60-fold greater, as shown in FIG. 17.

Cellular Uptake of Immunoliposomes Loaded with CF

CV1, Hc7, and MCF7 cells were grown on 25-mm round No. 1 glass coverslips for 24-48 hr. Immunoliposomes (0.025 mmol phospholipid/mL in 2 mL Hanks' Balanced Salt Solution (HBSS)) containing Rhod-PE, and encapsulating 100 mM CF were incubated with cells at 37° C. for 4 hr. Thereafter, the cells received three brief washes with $Ca^{2+}$- and $Mg^{2+}$-free HBSS containing 1 mM EDTA, and then maintained in $Ca^{2+}$- and $Mg^{2+}$-containing HBSS for fluorescence microscopy.

Cellular Uptake of Immunoliposomes Loaded with Nitroxide

Hc7 cells plated on replicate 60-mm plastic Petri dishes were incubated at 37° C. with immunoliposomes containing Rhod-PE, and encapsulating 150 mM nitroxide. Each 60-mm dish received immunoliposomes (0.025 µmol phospholipid/mL in 2 mL HBSS). At each time point, cells were washed with HBSS and then released from the plate with trypsin-EDTA. The cells were centrifuged at 1200 rpm for 3 min, and the pellet was washed twice with Ca2+- and Mg2+-free HBSS containing 1 mM EDTA. After the final wash, the pellet was resuspended in 400 µL normal HBSS. Cells were lysed with 120 µM digitonin and sonicated for 1 min. Cell-associated nitroxide and Rhod-PE were analyzed spectroscopically. The nitroxide concentration in each 400-µL sample was determined using a standard curve of spectral intensity vs. nitroxide concentration. The average intracellular nitroxide concentration was then estimated through volumetric calculations shown in FIG. 16. Average Hc7 cell volume was determined independently by confocal and transmitted light microscopy (A, error bars represent S.E.M.). Volumetric determination from 3-D reconstructions of confocal microscopic image slices yielded an average volume of 2.50 pL per cell (n=95, representative reconstruction shown in panel B). Likewise, measuring the diameter of spherical, trypsinized Hc7 cells using light microscopy gave an average volume of 2.68 µL per cell (n=68, representative image shown in panel C).

For confocal microscopic measurements, Hc7 cells were cultured on No. 1 glass coverslips and stained with Calcein-AM for 30 minutes at room temperature. Plates were washed with PBS and imaged on a laser-scanning confocal microscope (LSM510, Carl Zeiss, Oberkochen, Germany). Excitation used 488-nm emission from an argon-ion laser, and emission was passed through a 505-nm long-pass filter prior to photometric quantitation. Images were captured on an array-photomultiplier tube. Z-axis slices were obtained at 1 µm intervals. Volumetric measurements were made in Velocity 5.1 (Improvision/Perkin Elmer, Waltham, Mass.) using algorithms supplied with the program.

For transmitted light microscopy, Hc7 cells were trypsinized and suspended in PBS. Suspensions were plated on No. 1 glass coverslips and immediately imaged with transmitted light on an inverted epifluorescence microscope. Cell diameters were measured in Adobe Photoshop CS3 and referenced to a previously-measured length standard under the same magnification.

EPR Spectroscopy

A quartz flat-cell cuvette was used for acquisition of EPR spectra in an X-band spectrometer (E-109, Varian Associates, Palo Alto, Calif.) at the following settings: microwave power, 20 mW; frequency, 9.55 GHz; field center, 3335 G; modulation amplitude, 0.5 G; modulation frequency, 100 kHz; time constant, 0.5 sec. Field ranges from 8 to 80 G were scanned at 26.7 G/sec. Data acquisition was through EWWIN software (Scientific Software Services, Plymouth Mich.). Reported spectral intensities are the amplitude of the center peak in the nitroxide triplet spectrum.

Fluorescence Spectroscopy

Fluorescence spectra were recorded on a dual-excitation spectrofluorometer (model CMIT-101, SPEX Industries, Metuchen, N.J.). Instrument control and data acquisition were performed with Datamax software (Galactic Industries Corporation, Salem, N.H.). Emission and excitation spectra were acquired to determine optimal wavelength settings for Rhod-PE ($\lambda_{ex}$=550 nm, $\lambda_{em}$=588 nm).

Fluorescence Microscopy

Fluorescence images were acquired on an inverted epifluorescence microscope (Eclipse TE200, Nikon Corp, Tokyo, Japan) equipped with a 40× oil-immersion objective (Super Fluor, NA 1.4, Nikon). Excitation light was delivered by a xenon source coupled to a monochromator (PolyChrome II, TILL Photonics, Gräfelfing, Germany). Fluorescence was passed through an appropriate bandpass filter before capture by a CCD camera (CoolSnap HQ, Roper Scientific, Tucson, Ariz.). Instrument control, image acquisition and analysis were performed with MetaFluor software (Molecular Devices, Downingtown, Pa.).

Example 1—Glass Tubes Used as Imaging Phantom Device

Figure 4:
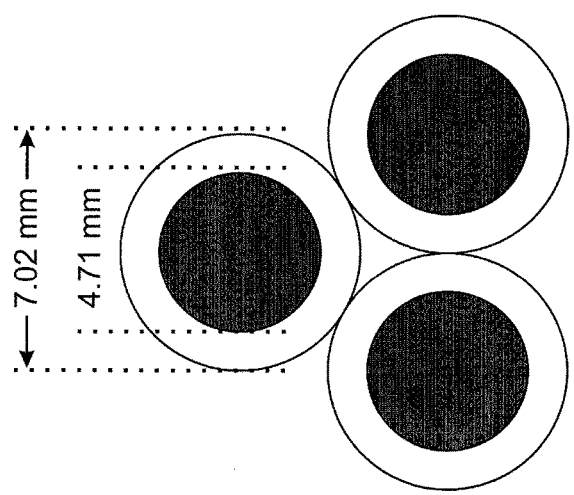
FIG. 4 is a schematic representation of a three-glass tube imaging phantom, wherein the loaded cells are placed within each tube.
Figure 5:
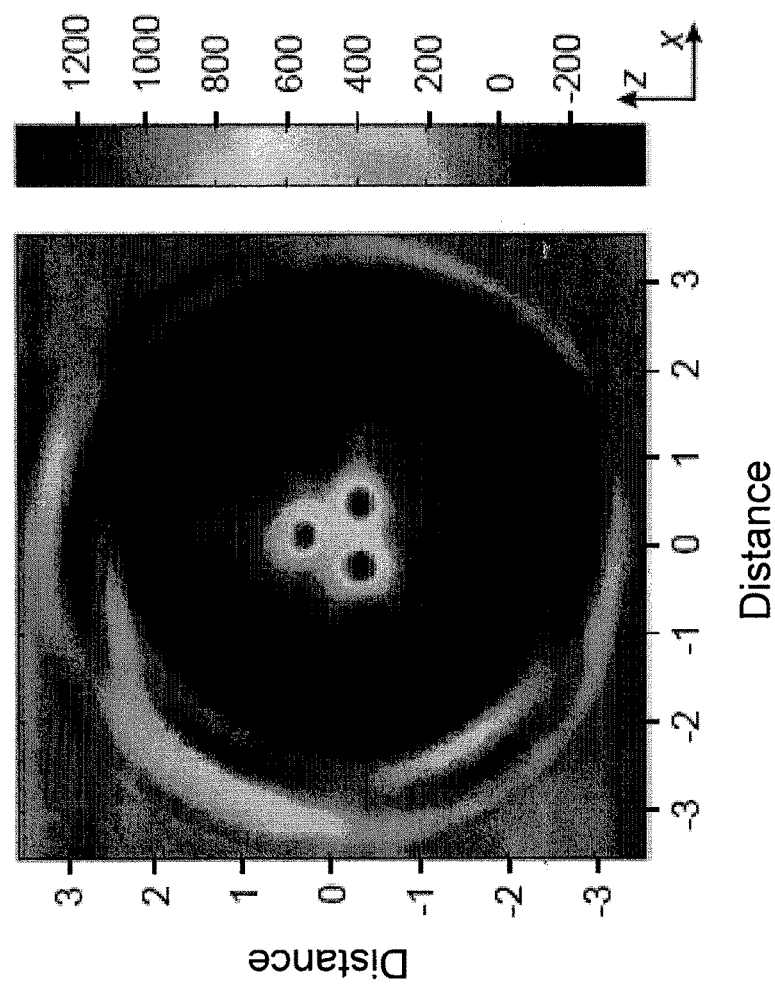
FIG. 5 shows the EPR image of a glass tube imaging phantom of FIG. 4 filled with cells loaded with nitroxide [3] from FIG. 1.

An imaging phantom was fabricated that comprises three identical glass tubes, each with an inner diameter of 4.71 mm and an outer diameter of 7.01 mm, as shown in FIG. 4. With their long axes aligned in parallel, the tubes were bundled in an equilateral triangular arrangement. Each tube received ~200 µl of sample, which spanned ~11.5 mm of the length of the tube. Plugs fabricated from hydrophilic polyvinylsiloxane dental impression material (GC Dental Products, Kasugai, Japan) were placed at the two ends of each tube, to fix the sample in the middle. To stabilize the triangular geometry, the tubes were placed in a precast cylindrical polyvinylsiloxane mold. FIG. 5 is a 2D EPR image in the X-Z plane of the imaging phantom shown in FIG. 4, which shows the cross-sections of the three cylinders each filled with cells that were loaded with nitroxide intracellularly. The image was reconstructed from data obtained by taking one spectral projection along each of 99 azimuthal angles in the X-Z plane. Three distinct circular regions of high intensity are visible. The known geometry and dimensions of the phantom are clearly reflected in the nitroxide image where the diameter of each circular signal matches that of each tube's inner diameter.

Example 2—Agarose Implant

Figure 6:
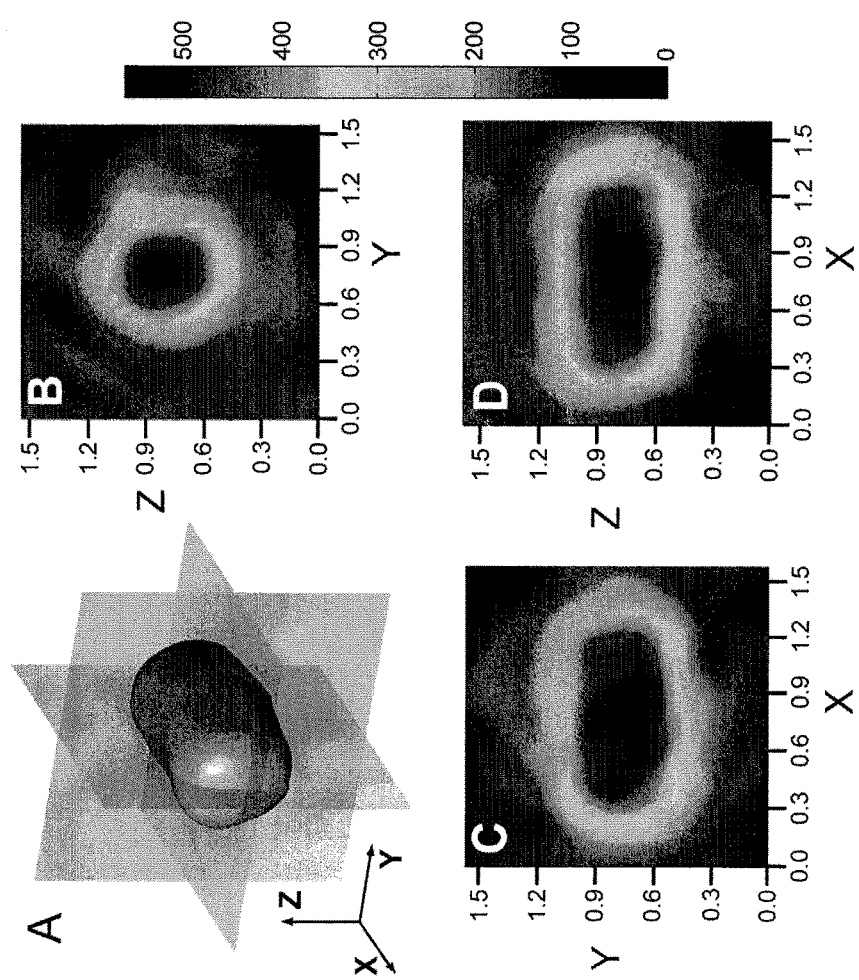
FIG. 6 shows an in vivo EPR image of a cylindrical, nitroxide-impregnated agarose implant in a mouse. (A)

FIG. 6 shows the EPR image of an agarose cylinder impregnated with 400 µM nitroxide and surgically implanted in a mouse.

Example 3—Hc7 Cells Derived from the MCF7 Breast Tumor Line Express High Levels of HER2 at the Plasma Membrane The human epidermal growth factor receptor 2 (HER2) is a 185 kDa receptor-tyrosine-kinase (RTK) that is related to the erbB receptor (King et al, 1985). It is highly overexpressed in some breast, ovarian, and non-small-cell lung cancers (Shepard et al, 1991). Approximately 30% of primary breast tumors exhibit HER2 overexpression (Kraus et al, 1987; Slamon et al, 1987), which is associated with cell proliferation, tumor progression (Marx et al, 1990), and poor clinical prognosis (Slamon et al, 1987). Therefore, HER2 has become an important target for diagnostics and therapeutics. One major therapeutic advance has been the development of humanized monoclonal antibodies against HER2 (e.g. trastuzumab). Trastuzumab binds the extracellular domain of the HER2 receptor and inhibits tumor progression through several mechanisms. Binding of HER2 by trastuzumab potentially inhibits receptor heterodimerization, which is required for RTK signaling (Schmitz & Ferguson, 2009). Importantly, it also induces antigen internalization, and intracellular sequestration limits receptor activation (Baselga et al, 2001; Sliwkowski et al, 1999; Yarden, 2001).

While trastuzumab itself has therapeutic activity, it has garnered attention as a targeting agent for HER2. The receptor-mediated endocytosis of HER2 observed after trastuzumab binding makes it an ideal targeting agent for delivery of xenobiotics to HER2-expressing cells. Antibody-mediated targeting of HER2 has been used to deliver several types of imaging diagnostics to HER2-overexpressing tumor cells. Heretofore, approaches for cellular delivery generally involved conjugating imaging probes directly to the antibody, including near-infrared fluorophores for in vivo optical imaging (Ogawa et al, 2009), radionuclides for positron emission tomography (Orlova et al, 2009), and superparamagnetic iron oxide nanoparticles for magnetic resonance imaging (MRI) (Chen et al, 2009).

To provide a testing model that exhibited an increase of HER-2 receptors, MCF7 breast tumor cells were stably transfected to overexpress the HER2 receptor. The resulting Hc7 transfectants were analyzed by western blot for HER2 expression, as shown in FIG. 10. Although Hc7 cells exhibit a high level of total HER2 expression compared to MCF7 cells, western blotting does not provide information regarding subcellular localization of protein.

Immunoliposomes can only target receptors that are accessible from the extracellular volume, thus the relative amount of HER2 localized at the plasma membrane must also be determined, as shown in FIG. 11. Hc7, MCF7, and CV1 cells were fixed with paraformaldehyde in PBS (final pH 7.4) without detergents. Cells were immunostained with trastuzumab as the primary antibody, and a FITC-conjugated, Fab-specific secondary antibody.

Immunolabeled cells were analyzed by fluorescence microscopy. As can be seen in FIG. 11A, the Hc7 cells show high HER2 expression at the cell surface, whereas untransfected MCF7 cells show only very feeble HER2 expression. For quantitation of immunofluorescence, CV1 cells served as the control for non-specific labeling, because they are African Green Monkey kidney epithelial cells, and therefore do not express the exclusively-human HER2 receptor. Fluorescence from CV1 cells was used to correct fluorescence intensities from the Hc7 and MCF7 cells. Notably, Hc7 cells exhibit ~25-200 times greater FITC fluorescence than MCF7 cells at the plasma membrane (t-test, $p<0.01$) (FIG. 11A). Hc7 cells express high levels of HER2 at the plasma membrane and thus are well-suited for immunoliposomal targeting approaches.

Example 4—Trastuzumab Fab' Fragments Retain Antigen-Binding Ability

Intact trastuzumab readily binds HER2 with high specificity, but attachment to liposomes requires proteolytic cleavage and reduction of the antibody to form the cross-linkable thiol-exposed Fab' fragment. To assess whether the process of generating Fab' fragments alters the binding capability or selectivity of trastuzumab, Hc7, MCF7, and CV1 cells were immunostained as outlined above, with the exception that primary antibodies were Fab' fragments whose exposed reactive thiol groups had been inactivated with maleimide (FIG. 12). Hc7 cells still exhibit ~35-100 times greater FITC fluorescence than MCF7 cells (t-test $p<0.01$). When an ANOVA is performed on the combined data from FIGS. 11A and 12A, post-hoc analysis confirms the previous t-test results—regardless of which primary antibody was used, immunofluorescence differed significantly between Hc7 and MCF7 cells.

In contrast, within each cell line, immunofluorescence was not significantly affected by the choice of intact trastuzumab IgG or the Fab' fragment as the primary antibody (ANOVA $F_{3,60}=108.48$). Therefore, trastuzumab Fab' fragments bind HER2 as avidly and selectively as intact trastuzumab IgG, and thereby providing immunoliposomes that target the receptor.

Example 5—Immunoliposomal Delivery of Fluorescent Probes Generate Intense Intracellular Fluorescence in HER2-Overexpressing Cells Anti-HER2 immunoliposomes incorporating Rhod-PE and encapsulating 100 mM CF were incubated with Hc7, MCF7, or CV1 cells for 4 hr. Cells were rinsed three times with Ca2+- and Mg2+-free HBSS containing 1 mM EDTA, and then maintained in normal HBSS for fluorescence imaging (FIG. 13). As can be seen in panels a-c of FIG. 13, Hc7 cells exhibit bright intracellular CF fluorescence as the result of immunoliposome internalization and subsequent de-quenching of the encapsulated CF. The Hc7 cells also show intense, more punctuate, intracellular Rhod-PE fluorescence, reflecting incorporation of Rhod-PE from the immunoliposomes into intracellular membranes. In contrast, MCF7 cells, which express only physiological levels of HER2, endocytose few immunoliposomes and thus show very feeble intracellular CF and Rhod-PE (FIG. 13, panels d-f). Lastly, CV1 cells, which do not express HER2, have no detectable fluorescence signals (FIG. 13, panels g-i). These results indicate that endocytic uptake of immunoliposomes is dependent on cellular HER2 expression, and that it is possible to generate intense intracellular signals selectively in HER2-overexpressing breast tumor cells.

Example 6—Hc7 Cells Achieve High Intracellular Nitroxide Concentrations Through Endocytosis of Immunoliposomes Replicate dishes of Hc7 cells were incubated at 37° C. with immunoliposomes incorporating Rhod-PE, and encapsulating 150 mM nitroxide. At various time points, cells were trypsinized and washed with Ca2+- and Mg2+-free PBS containing 1 mM EDTA. The amount of nitroxide [3] (See FIG. 1) and Rhod-PE associated with the cells was determined spectroscopically as described in hereinabove. Cell-associated nitroxide and Rhod-PE initially increased in parallel with time of incubation as shown in FIG. 14, as expected from endocytic uptake of liposomes and their luminal contents. Between 2 and 6 hrs, there was a persistent, cell-associated nitroxide signal which peaks at ~750 µM. By 9 hr, intracellular nitroxide concentration had declined to ~350 uM, while cell-associated Rhod-PE was unchanged from the level observed at 6 hr. This suggests that beyond 6 hrs, endocytosis became very slow. As a result, without continual uptake of liposomes for replenishment, cellular transport processes that extrude nitroxides (Rosen et al, 2005) dominated, leading to a net loss of intracellular nitroxide signal. Even so, intracellular nitroxide concentrations were in the several hundred micromolar range, which is ample for and visible by EPRI thereby permitting cellular imaging studies of Hc7 cells. The results set forth herein demonstrate that liposomes encapsulating quenched fluorophores and nitroxides can be specifically directed to, and generate detectable intracellular spectral signals in, Hc7 cells.

The results in FIG. 13 demonstrate that anti-HER2 immunoliposomes are avidly and selectively endocytosed by Hc7 cells. After subsequent liposomal lysis and release of the quenched fluorophores into the much larger intracellular volume, de-quenching results in an intense intracellular CF fluorescence signal. Targeting liposomes with trastuzumab Fab' fragments allows cellular uptake to occur in proportion to the HER2 expression level of that cell type. MCF7 and CV1 cells, which have physiological or no HER2 expression, respectively, take up immunoliposomes either very feebly or not at all, and thus do not generate robust spectral signals intracellularly, such as in the Hc7 cells.

Example 7—Stealth Liposomes

Stealth liposomes were fabricated according to FIG. 20, wherein poly(ethyleneglycol) (PEG) was attached to the surface of the liposome. The liposomes encapsulate the imaging probe (nitroxide) at a concentration sufficient to cause concentration-dependent quenching of their spectroscopic signal. When the liposomes were taken up by the cells and broken open intracellularly, the encapsulated probes were diluted into a much larger cellular volume and the quenching was relieved (de-quenching) to generate a robust spectral signal inside the cells that have taken up the liposomes. Viewing FIG. 19 it is evident that the stealth liposomes stay in circulation much longer than liposomes bearing no PEG. Greater persistence in circulation means more access to tumor tissue. Clearly, the free nitroxides injected into the vasculature were rapidly cleared from the circulation in minutes.

A sample of blood was drawn at 24 hours after injections of the stealth liposomes encapsulating nitroxide at high concentration (150 mM). Before lysis with detergent, the EPR spectral signal was feeble, however, after the detergent lysis, the EPR signal was robust as shown in the right-hand graph of FIG. 19. This shows that even after 24 hours in circulation, the stealth liposomes remained intact and there was little loss or leakage of nitroxide from the liposomal lumen. Thus, the PEGylated immunoliposomes are good, stable vehicles for in vivo delivery of EPR imaging probes as shown in FIGS. 19 and 21.

Hc7 cells overexpressing HER-2 receptor were implanted into the flanks of SCID mice to form tumors that grew rapidly during a six week period as shown in FIG. 11. When the stealth liposomes of the present invention, having a Fab' with affinity for the HER-2 receptor, bind to the HER-2 receptor, the complex is endocytosed and lysed within the cell. When the stealth immunoliposomes encapsulate the near-infrared fluorescent dye, indocyanine green (ICG), at high concentration, liposome-mediated delivery of ICG to the tumor cells in the mouse can be visualized through in vivo fluorescence imaging (FIG. 21; image taken 4 hours after intravenous injection of liposomes). Avid uptake of the ICG-encapsulating liposomes resulted in bright fluorescence in the tumors (marked by arrows in FIG. 21).

As expected, ICG fluorescence was also seen in the abdomen which is attributed to the liver and spleen, both of which are major organs that remove the immunoliposomes from the circulation.

Using immunoliposomes of the present invention to direct fluorescent and EPR imaging agents to HER2-overexpressing breast tumors has inherent advantages. Background from unendocytosed liposomes is easily minimized by exploiting the self-quenching of the probes. In contrast to targeting mechanisms where the antibody is directly labeled with molecular probes, immunoliposomes encapsulating high concentrations of molecular probes maximize the ability of cells to accumulate high concentrations of imaging agents. The consequence is greatly improved signal-to-noise ratios (SNR), which is critical in EPRI, as in any imaging modality. For example, when each internalized antibody is coupled to a liposome that has an outer diameter of 100 nm, and that encapsulates 150 mM CF or nitroxide, each endocytosed liposome delivers ~34,000 probe molecules. The consequent signal amplification is essential for EPRI. Immunoliposomes enable Hc7 cells to accumulate a maximal intracellular nitroxide concentration of ~750 µM (FIG. 14). As shown in FIG. 14, intracellular concentration of about 400 µM nitroxide is readily detectable with high contrast and excellent SNR when using in vivo EPRI phantom implants.

Using immunoliposomes to deliver nitroxides to HER2-overexpressing tumors in vivo requires additional considerations. First, liposomes are cleared from the circulation by the reticulo-endothelial system (RES) (Liu & Liu, 1996), and must be engineered to evade such clearance mechanisms in vivo. Incorporating into the liposomes a small proportion of lipid conjugated to poly(ethyleneglycol) (PEG) retards clearance by the RES (Woodle & Lasic, 1992). The longer circulation times exhibited by sterically-stabilized, "PEGy-lated" liposomes enhance their targeting potential in vivo. Second, since liposomes must target tumors from the circulation, their ultimate uptake into tumor cells depends on tumor vascularization. While previous studies examining the pharmacodynamics of liposomes in tumor models suggests a relatively uniform micro-distribution of immunoliposomes within tumors (Kirpotin et al, 2006), the macro-distribution could be inhomogeneous due to any necrosis toward the center of tumor. Thus, it is possible that only some fraction of the tumor volume is accessible to liposomes. In light of the possibility that only a fraction of the cells in a tumor may be accessible to liposomes from the circulation, it is possible that despite the very high intracellular concentrations potentially achievable with immunoliposomal delivery, the total amount of nitroxide molecules throughout the entire volume of the tumor may still be modest.

Achieving greater SNR in EPRI can be accomplished by delivering greater quantities of nitroxides to cells, and optimizing the intrinsic SNR of the nitroxide itself. Greater quantities of nitroxides can be delivered by liposomes which have larger luminal volumes or encapsulate higher concentrations of nitroxides. Liposomes with 100-nm outer diameter are already close to optimal for in vivo delivery—increasing the diameter results in increased circulatory clearance and reduced extravasation, both of which offset the advantage of the larger luminal volume (Allen et al, 2006; Charrois & Allen, 2003).

Fortunately, the performance of nitroxides as EPR imaging agents can be improved through rational design and by synthesizing nitroxides that are zwitterionic at physiologic pH. Such nitroxides are preferably highly water-soluble and do not require counter-ions, which normally increases the osmolarity of the encapsulated solution without any corresponding benefit to SNR. Thus zwitterionic nitroxides can be encapsulated at 300 mM—twice the concentration of the nitroxide presented in FIG. 14, which bears a net anionic charge at physiological pH. Additional improvement of SNR can be achieved by synthesizing nitroxides that are deuterium- and $^{15}$N-substituted. Such nitroxides have narrower spectral peaks and, as a result, larger peak amplitudes, as shown in FIG. 9. These two improvements will significantly enhance the feasibility of visualizing Hc7 tumors in vivo by EPR imaging.

Example 8—Synthesis of Isotopic-Substituted Nitroxides as Shown in FIG. 22

The synthesis of 3-carboxy 2,2,5,5-tetra($^2$H$_3$)methyl-1-(3, 4,4-$^2$H$_3$,1-$^{15}$N)pyrrolidinyloxyl [6], is described below, wherein isotopic substitution with $^{15}$N and $^2$H improves detection limits and signal-to-noise ratio (SNR), as shown in FIG. 9. The rationale for isotopic substitution is straightforward because as shown in FIG. 9, in an isotopically unmodified nitroxide, hyperfine interaction with the spin-1 $^{14}$N nucleus splits the electron resonance into three spectral lines, each with roughly one-third the total signal intensity. Because EPRI measures the amplitude of only one spectral line, the signal contained in the other two lines is wasted. However, in the spin-½ $^{15}$N nucleus splits the nitroxide resonance into only two lines, each of which contains 50% more signal than any line in the $^{14}$N EPR spectrum. Additionally, in isotopically unmodified nitroxides, hyperfine interactions with $^1$H nuclei broaden the EPR spectral lines, with corresponding reduction of peak amplitudes. Complete isotopic substitution with $^2$H, which has a weaker nuclear magnetic moment, reduces line broadening and thereby increases spectral peak amplitude and SNR. Lastly, O$_2$ concentrations are estimated from the width of the EPR spectral lines and the spectra line width is much narrower in the isotopically substituted nitroxide thereby providing for increase sensitivity for $O_2$ measurement in vivo.

4-Oxo-2,2,6,6-tetra($^2H_3$)methyl-(3,3,5,5-$^2H_4$, 1-$^{15}$N)piperidine [2]. This compound was prepared following the general procedure of Lin, et al. (1990) with minor modifications. Deuterium exchange of $^{15}NH_4Cl$ (10.0 g, 98%), forming $^{15}N^2H_4Cl$, was accomplished by dissolving $^{15}NH_4Cl$ in $D_2O$ (15 mL). Then, the solution was evaporated to dryness under an $N_2$ atmosphere. This procedure was repeated three more times.

In a dry box with a positive $N_2$ flow, $^{15}N^2H_4Cl$ (3.5 g, 60 mmol) was added to a 250-mL round bottom flask, which contained anhydrous $Na_2CO_3$ (3.18 g, 30 mmol) and oven-dried MgO (3.0 g, 75 mmol). Once completed, acetone-$d_6$ (12.5 mL, 150 mmol; 99.9%) was introduced into the flask. The flask was capped with a rubber septum, heated for 3 days in an oil bath at 50° C., and then allowed to cool. Then, acetone-$d_6$ (20 mL) was added to the flask and the resulting mixture was filtered. The filter cake was crushed into a fine powder, washed with dry ether and acetone-$d_6$ (1:1 mixture, 20 mL) and again filtered; this procedure was repeated three more times. The combined filtrates were concentrated on a rotary evaporator to give a red liquid (5.5 g), a portion of which was distilled to yield a yellow liquid (bp 60-64° C. at 12 mm Hg), which solidified upon cooling. In trial runs, we found that distillation of [2] did not significantly affect the yield of [3]; therefore, crude [2] was used for the next reaction without further purification.

4-Oxo-2,2,6,6-tetra($^2H_3$)methyl-1-(3,3,5,5-$^2H_4$,1-$^{15}$N)piperidinyloxyl [3]. To a solution of crude 4-oxo-2,2,6,6-tetra ($^2H_3$)methyl-(1,3,3,5,5-$^2H_5$,1-$^{15}$N)piperidine [2] (5.5 g, 34 mmol) dissolved in $D_2O$ (60 mL), was added oven-dried $Na_4EDTA$ (0.55 g, 1.5 mmol) and oven-dried $Na_2WO_4$ (0.55 g, 1.7 mmol). Upon dissolution of the salts, $D_2O_2$ (30% in $D_2O$, 6 mL) was added and the reaction was allowed to proceed in the dark for 8-10 days. The reaction mixture was filtered and extracted with ether (3×50 mL). The ether solution was first washed with cold dilute $^2HCl$ (10% in $D_2O$, 2×20 mL) and then a saturated solution of $Na_2CO_3$ in $D_2O$ (10 mL). The remaining ether solution was dried over anhydrous $MgSO_4$, and then evaporated to dryness. This nitroxide was chromatographed using silica gel, eluting with hexane:ether (1:1) to afford 4-oxo-2,2,6,6-tetra($^2H_3$)methyl-1-(3,3,5,5-$^2H_4$,1-$^{15}$N)piperidinyloxyl [3], as red oil, which solidified in the cold (2.8 g, 51% yield). IR ($CHCl_3$): 1720 $cm^{-1}$ (C=O). Anal. calculated for $C_9{}^2H_{16}{}^{15}NO_2$: C, 57.69; $^2H$, 8.61; $^{15}N$, 7.48. Found: C, 57.57; $^2H$, 8.58; $^{15}N$, 7.40.

4-Oxo-2,2,6,6-tetra($^2H_3$)methyl-1-($^2H$)hydroxy-(3,3,5,5-$^2H_4$,1-$^{15}$N)piperidine ($^2H$) hydrochloride [4]. This compound was prepared following the general procedure of Marc and Pecar (1995) with minor modifications. 4-Oxo-2, 2,6,6-tetra($^2H_3$)methyl-1-(3,3,5,5-$^2H_4$,1-$^{15}$N)piperidinyloxyl [3] (2.8 g, 15 mmol) was dissolved in $CH_3O^2H$ (30 mL) and 5% Pd/C (50 mg) was added. Deuterium (99%) was slowly bubbled into the reaction for several min and the flask was sealed. Over the next several h, $D_2$ was added periodically to the reaction. The following day, the reaction was filtered through Celite and the remaining solution, which was colorless, was acidified with 4 M $^2HCl$ (in $D_2O$, 2.5 mL). The colorless filtrate was reduced to dryness on a rotary evaporator. The residue was washed with dry ether (2×20 mL) to remove any remaining nitroxide and dried, in vacuo, to yield 4-oxo-2,2,6,6-tetra($^2H_3$)methyl-1-($^2H$)hydroxyl-(3,3,5,5-$^2H_4$,1-$^{15}$N)piperidine ($^2H$)hydrochloride [4], as a white solid (2.7 g, 80% yield).

3-Bromo-4-oxo-2,2,6,6-tetra($^2H_3$)methyl-1-(3,5,5-$^2H_3$,1-$^{15}$N)piperidinyloxyl [5]. This compound was prepared following the procedure of Sosnovsky and Cai (1995) with minor modifications. To a stirred solution of 4-oxo-2,2,6,6-tetra($^2H_3$)methyl-1-($^2H$)hydroxyl-(3,3,5,5-$^2H_4$,1-$^{15}$N)piperidine ($^2H$)hydrochloride [4] (2.7 g, 11.9 mmol) in $CHCl_3$ (25 mL) was added a solution of bromine (2.14 g, 11.9 mmol) in $CHCl_3$ (10 mL), drop-wise over 45 min at room temperature. Then, the reaction mixture was stirred for an additional 2.5 h at this temperature. Thereafter, a solution of $NaNO_2$ (1.85 g, 27 mmol) in $D_2O$ (10 mL) was added drop-wise over 10 min to the vigorously stirred reaction mixture. Stirring continued for another 15 min. The organic phase was washed with $D_2O$, dried over anhydrous $MgSO_4$, filtered, and evaporated to dryness under reduced pressure. The residue was purified on silica gel using hexane:ether (2:1), as the eluting solvent mixture. Fraction #1 is 3-bromo-4-oxo-2,2,6,6-tetra($^2H_3$)methyl-1-(3,5,5-$^2H_3$,1-$^{15}$N)piperidinyloxyl [5], whereas fraction #2 is starting material, nitroxide [3]. Re-reducing piperidinyloxyl [3] with 5% Pd/C (25 mg) and $CH_3O^2H$ (30 mL) followed by bromination/oxidation with $NaNO_2$, one can obtain piperidinyloxyl [5] in an overall yield of 64% (2.0 g). This compound was recrystallized from hexane, mp=81-82° C.; IR ($CHCl_3$): 1730 $cm^{-1}$ (C=O). Anal. calculated for $C_9{}^2H_{15}{}^{15}NBrO_2$: C, 40.75; $^2H$, 5.70; $^{15}N$, 5.28; Br, 30.13. Found: C, 41.39; $^2H$, 5.80; $^{15}N$, 5.35; Br, 30.48.

3-Carboxy-2,2,5,5-tetra($^2H_3$)methyl-1-(3,4,4-$^2H_3$,1-$^{15}$N)pyrrolidinyloxyl [6]. The general procedure of Sosnovsky and Cai (1995) was used, with minor modifications. A solution of KOD (1 M in $D_2O$, 5 mL) was added to 3-bromo-4-oxo-2,2,6,6-tetra($^2H_3$)methyl-1-(3,5,5-$^2H_3$,1-$^{15}$N)piperidinyloxyl [5] (0.52 g, 2 mmol). Over the next 2 h of stirring at room temperature, nitroxide [5] dissolved in the KOD solution. The alkaline solution was extracted with ether (3×20 mL), cooled in an ice bath, and titrated to pH 3 with dilute $^2HCl$ (10% in $D_2O$). The acidic solution was extracted with ether (3×20 mL); this extract was dried over anhydrous $MgSO_4$, filtered, and evaporated under reduced pressure to yield 3-carboxy-2,2,5,5-tetra($^2H_3$)methyl-1-(3,4, 4-$^2H_3$,1-$^{15}$N)pyrrolidinyloxyl [6] as a yellow solid (0.25 g, 61%). Recrystallization from chloroform/hexane gave a yellow powder, mp=190-194° C. (with decomposition); IR ($CHCl_3$): 3500 $cm^{-1}$ (broad peak, Ohio), 1711 $cm^{-1}$ (C=O).

3-Acetoxymethoxycarbonyl-2,2,5,5-tetra($2H_3$)methyl-1-(3,4,4-$^2H_3$,1-$^{15}$N)pyrrolidinyloxyl [7]. Bromomethyl acetate (0.044 g, 0.03 mL, 0.33 mmol) was added to a solution of 3-carboxy-2,2,5,5-tetra($^2H_3$)methyl-1-(3,4,4-$^2H_3$,1-$^{15}$N) pyrrolidinyloxyl [6] (0.050 g, 0.30 mmol) and $K_2CO_3$ (0.070 g, 0.50 mmol) in acetonitrile (dried over CaH, 10 mL). The reaction was stirred overnight at room temperature. Thereafter, this mixture was filtered through Celite, and the remaining solution was evaporated to dryness. The resultant oil was chromatographed on silica gel, eluting with hexane: ethyl acetate (5:1). After evaporation, the remaining thick oil was crystallized from hexane, yielding 3-acetoxymethoxycarbonyl-2,2,5,5-tetra($^2H_3$)methyl-1-(3,4,4-$^2H_3$,1-$^{15}$N)pyrroldinyloxyl [7] as a yellow solid (0.10 g; 71%), with mp=77-78° C.; IR ($CHCl_3$): 1763 $cm^{-1}$ (C=O). Anal. calculated for $C_{12}{}^2H_{15}{}^1H_5{}^{15}NO_5$: C, 52.52; $^2H+^1H$, 7.35; $^{15}N$, 5.10. Found: C, 52.76; $^2H+^1H$, 7.42; $^{15}N$, 5.12.

Example 9—Synthesis of Isotopic-Substituted Nitroxides as Shown in FIG. 23

Methyl 2,2,6,6-tetra($^2H_3$)methyl-1-(3,3,5,5-$^2H_4$,1-$^{15}$N)piperidinyloxyl-4-ideneacetate [8]. n-Butyllithium (2.5 M in hexane, 2.9 mL, 7.1 mmol., Aldrich Chemical Company) was added to a three-necked flask containing tetrahydrofuran (50 mL, freshly distilled over lithium aluminum hydride) at −5° C. under a $N_2$ atmosphere. Then, diisopropylamine (1.0 mL, 7.1 mmol.) in tetrahydrofuran (5 mL) was added, maintaining this temperature during the addition. Thereafter, the flask was immersed in a dry ice-acetone bath at −78° C. and methyl trimethylsilyl ($^2H_2$) acetate (1.2 mL, 7.1 mmol.) dissolved in tetrahydrofuran (20 mL) was added slowly, keeping the temperature of the reaction at −78° C. After the addition was complete, the reaction was stirred at this temperature for 20 min. Then, 4-oxo-2,2,6,6-tetra($^2H_3$) methyl-1-(3,3,5,5-$^2H_4$,1-$^{15}N$)piperidinyloxyl [3] (1.3 g, 7.1 mmol.) in tetrahydrofuran (20 mL) was added to the reaction, maintaining the temperature at −78° C. The mixture was stirred at this temperature for an additional 20 min, and it was then warmed to room temperature. At this point, cold dilute DCl (5%) was added, adjusting the pH to 3-4, and then the mixture was extracted with pentane:diethyl ether (1:1, 3-times). The combined organic solutions were washed with a solution of $Na_2CO_3$ saturated in $D_2O$, dried over anhydrous $Na_2SO_4$ and evaporated to dryness, affording thick red oil. This oil was chromatographed with silica gel, eluting with hexane:diethyl ether (4:1) to give methyl 2,2,6,6-tetra ($^2H_3$)methyl-1-(3,3,5,5-$^2H_4$,1-$^{15}N$)piperidinyloxyl-4-ideneacetate [8] (1.3 g, 75%, which was recrystallized from hexane, mp=57-58° C.). IR (CHCl$_3$): 1713 (C=O), 1661 (C=C) cm$^{-1}$.

Acetoxymethoxy 2,2,6,6-tetra($^2H_3$)methyl-1-(3,3,5,5-$^2H_4$,1-$^{15}N$)piperidinyloxyl ideneacetate [10]. To a methanolic (CH$_3$OD) solution (25 mL) of methyl 2,2,6,6-tetra($^2H_3$)methyl-1-(3,3,5,5-$^2H_4$,1-$^{15}N$)piperidinyloxyl-4-ideneacetate [8] (1 g, 4.1 mmol.) was add a solution of KOD (1 M in D$_2$O, 2 mL). The reaction was warmed <40° C. for 6 hr, following the hydrolysis by TLC (silica gel plates and hexane:ether (1:1)). Upon cooling to room temperature, the reaction mixture was evaporated to dryness, in vacuo. Then, D$_2$O (50 mL) was added, and the mixture was extracted with CH$_2$Cl$_2$ (25 mL, 3-times). The aqueous solution was then cooled in an ice bath, bringing the pH of the solution to 3-4 with dilute $^2$HCl (10%). The solution was then extracted with ether, dried over anhydrous MgSO$_4$ and evaporated to dryness. The crude oil, 2,2,6,6-tetra($^2H_3$)methyl-1-(3,3,5,5-$^2H_4$,1-$^{15}N$)piperidinyloxyl-4-ideneacetic [9], was used to form the acetoxymethyl ester without further purification.

To the crude acid, 2,2,6,6-tetramethyl-1-piperidinyloxyl-4-ideneacetic acid [9] (1.2 g, 5.3 mmol.) dissolved in acetonitrile (5 mL) was introduced K$_2$CO$_3$ (1.4 g, 10.2 mmol.). This reaction was stirred at room temperature for 10 min at which point bromomethyl acetate (0.81 g, 0.52 mL, 5.3 mmol., Aldrich Chemical Company) was added and the reaction was stirred overnight at this temperature. To this mixture, CH$_2$Cl$_2$ (50 mL) was added and the solution was washed with D$_2$O (10 mL, 3-times). The organic solution was dried over anhydrous Na$_2$SO$_4$ and evaporated to dryness, affording thick red oil. This oil was chromatographed using silica gel, and eluted with hexane:ethyl acetate (12:50 mL) to give acetoxymethoxycarbonyl 2,2,6,6-tetra($^2H_3$) methyl-1-(3,3,5,5-$^2H_4$,1-$^{15}N$)piperidinyloxyl ideneacetate [10], as thick oil (0.64 g, 50%). IR (CHCl$_3$): 1757, 1733 (C=O), 1653 (C=C) cm$^{-1}$.

REFERENCES

The contents of all references cited herein are incorporated by reference herein for all purposes.

Allen T M, Cheng W W, Hare J I, Laginha K M (2006) Pharmacokinetics and pharmacodynamics of lipidic nanoparticles in cancer. *Anticancer Agents Med Chem* 6: 513-23

Baselga J, Albanell J, Molina M A, Arribas J (2001) Mechanism of action of trastuzumab and scientific update. *Semin Oncol* 28: 4-11

Burks S R, Barth E D, Halpern H J, Rosen G M, Kao J P (2009) Targeted delivery of electron paramagnetic resonance imaging probes through endocytosis of liposomes. *Biochim Biophys Acta*: Submitted Charrois G J, Allen T M (2003) Rate of biodistribution of STEALTH liposomes to tumor and skin: influence of liposome diameter and implications for toxicity and therapeutic activity. *Biochim Biophys Acta* 1609: 102-8

Chen T J, Cheng T H, Chen C Y, Hsu S C, Cheng T L, Liu G C, Wang Y M (2009) Targeted Herceptin-dextran iron oxide nanoparticles for noninvasive imaging of HER2/neu receptors using MRI. *J Biol Inorg Chem* 14: 253-60

Dreher M R, Elas M, Ichikawa K, Barth E D, Chilkoti A, Rosen G M, Halpern H J, Dewhirst M (2004) Nitroxide conjugate of a thermally responsive elastin-like polypeptide for noninvasive thermometry. *Med Phys* 31: 2755-62

Elas M, Ahn K H, Parasca A, Barth E D, Lee D, Haney C, Halpern H J (2006) Electron paramagnetic resonance oxygen images correlate spatially and quantitatively with Oxylite oxygen measurements. *Clin Cancer Res* 12: 4209-4217

Elas M, Bell R, Hleihel D, Barth E D, McFaul C, Haney C R, Bielanska J, Pustelny K, Ahn K H, Pelizzari C A, Kocherginsky M, Halpern H J (2008) Electron paramagnetic resonance oxygen image hypoxic fraction plus radiation dose strongly correlates with tumor cure in FSa fibrosarcomas. *Int J Radial Oncol Biol Phys* 71: 542-549

Halpern H J, Chandramouli G V, Barth E D, Yu C, Peric M, Grdina D J, Teicher B A (1999) Diminished aqueous microviscosity of tumors in murine models measured with in vivo radiofrequency electron paramagnetic resonance. *Cancer Res* 59: 5836-5841

Halpern H J, Spencer D P, Vanpolen J, Bowman M K, Nelson A C, Dowey E M, Teicher B A (1989) Imaging radio-frequency electron-spin-resonance spectrometer with high-resolution and sensitivity for in vivo measurements. *Review of Scientific Instruments* 60: 1040-1050

Kallioniemi O P, Kallioniemi A, Kurisu W, Thor A, Chen L C, Smith H S, Waldman F M, Pinkel D, Gray J W (1992) ERBB2 amplification in breast cancer analyzed by fluorescence in situ hybridization. *Proc Natl Acad Sci USA* 89: 5321-5

Kao J P, Barth E D, Burks S R, Smithback P, Mailer C, Ahn K H, Halpern H J, Rosen G M (2007) Very-low-frequency electron paramagnetic resonance (EPR) imaging of nitroxide-loaded cells. *Magn Reson Med* 58: 850-4

Khramtsov V V, Weiner L M, Grigoriev I A, Volodarsky L B (1982) Proton exchange in stable nitroxyl radicals. EPR study of the pH of aqueous solutions. *Chem Phys Lett*: 69-72

King C R, Kraus M H, Aaronson S A (1985) Amplification of a novel v-erbB-related gene in a human mammary carcinoma. *Science* 229: 974-6

Kirpotin D B, Drummond D C, Shao Y, Shalaby M R, Hong K, Nielsen U B, Marks J D, Benz C C, Park J W (2006) Antibody targeting of long-circulating lipidic nanoparticles does not increase tumor localization but does increase internalization in animal models. *Cancer Res* 66: 6732-40

Kraus M H, Popescu N C, Amsbaugh S C, King C R (1987) Overexpression of the EGF receptor-related proto-oncogene erbB-2 in human mammary tumor cell lines by different molecular mechanisms. *EMBO J.* 6: 605-10

Lin, Y. J.; Teicher, B. A.; Halpern, H. J., (1990) Synthesis Of 4-Protio-3-Carbamoyl-2,2,5,5-Tetraperdeuteromethyl-3-Pyrrolin-1-Yloxy (Mhctpo)—A Selectively Isotopically Labeled Compound For Use In T2 Spin Label Oxymetry. *J. Labelled Comp. Rad.*, 28, 621.

Liu F, Liu D (1996) Serum independent liposome uptake by mouse liver. *Biochim Biophys Acta* 1278: 5-11

Mamot C, Drummond D C, Greiser U, Hong K, Kirpotin D B, Marks J D, Park J W (2003) Epidermal growth factor receptor (EGFR)-targeted immunoliposomes mediate specific and efficient drug delivery to EGFR- and EGFRvIII-overexpressing tumor cells. *Cancer Res* 63: 3154-61

Marc, G.; Pecar, S., (1995) A Short Way To Esters Of 1-Oxyl-2,2,5,5-Tetramethylpyrrolidine-3-Carboxylic Acid By Favorski Rearrangement. *Syn. Commun.*, 20, 1015.

Marx D, Schauer A, Reiche C, May A, Ummenhofer L, Reles A, Rauschecker H, Sauer R, Schumacher M (1990) c-erbB2 expression in correlation to other biological parameters of breast cancer. *J Cancer Res Clin Oncol* 116: 15-20

Ogawa M, Kosaka N, Choyke P L, Kobayashi H (2009) In vivo molecular imaging of cancer with a quenching near-infrared fluorescent probe using conjugates of monoclonal antibodies and indocyanine green. *Cancer Res* 69: 1268-72

Orlova A, Wallberg H, Stone-Elander S, Tolmachev V (2009) On the selection of a tracer for PET imaging of HER2-expressing tumors: direct comparison of a 1241-labeled affibody molecule and trastuzumab in a murine xenograft model. *J Nucl Med* 50: 417-25

Park J W, Hong K, Kirpotin D B, Colbem G, Shalaby R, Baselga J, Shao Y, Nielsen U B, Marks J D, Moore D, Papahadjopoulos D, Benz C C (2002) Anti-HER2 immunoliposomes: enhanced efficacy attributable to targeted delivery. *Clin Cancer Res* 8: 1172-81

Park J W, Kirpotin D B, Hong K, Shalaby R, Shao Y, Nielsen U B, Marks J D, Papahadjopoulos D, Benz C C (2001) Tumor targeting using anti-her2 immunoliposomes. *J Control Release* 74: 95-113

Rosen G M, Burks S R, Kohr M J, Kao JP (2005) Synthesis and biological testing of aminoxyls designed for long-term retention by living cells. *Org Biomol Chem* 3: 645-8

Schmitz K R, Ferguson K M (2009) Interaction of antibodies with ErbB receptor extracellular regions. *Exp Cell Res* 315: 659-70

Shen J, Liu S, Miyake M, Liu W, Pritchard A, Kao J P Y, Rosen G M, Tong Y and Liu K J (2006) Use of 3-acetoxymethoxcarbonyl-2,2,5,5-tetramethyl-1-pyrrolidinyloxyl as an EPR oximetry probe: Potential for in vivo measurement of tissue oxygenation in mouse brain. *Magn Reson Med* 55:1433-40

Shepard H M, Lewis G D, Sarup J C, Fendly B M, Maneval D, Mordenti J, Figari I, Kotts C E, Palladino M A, Jr., Ullrich A, et al. (1991) Monoclonal antibody therapy of human cancer: taking the HER2 protooncogene to the clinic. *J Clin Immunol* 11: 117-27

Slamon D J, Clark G M, Wong S G, Levin W J, Ullrich A, McGuire W L (1987) Human breast cancer: correlation of relapse and survival with amplification of the HER-2/neu oncogene. *Science* 235: 177-82

Sliwkowski M X, Lofgren J A, Lewis G D, Hotaling T E, Fendly B M, Fox J A (1999) Nonclinical studies addressing the mechanism of action of trastuzumab (Herceptin). *Semin Oncol* 26: 60-70

Sosnovsky. G.; Cai, Z. W., (1995) A Study Of The Favorskii Rearrangement With 3-Bromo-4-Oxo-2,2,6,6-Tetramethylpiperidin-1-Oxyl. *J. Org. Chem.*, 60, 3414.

Szollosi J, Balazs M, Feuerstein B G, Benz C C, Waldman F M (1995) ERBB-2 (HER2/neu) gene copy number, p185HER-2 overexpression, and intratumor heterogeneity in human breast cancer. *Cancer Res* 55: 5400-7

Utsumi H, Yamada K, Ichikawa K, Sakai K, Kinoshita Y, Matsumoto S, Nagai M (2006) Simultaneous molecular imaging of redox reactions monitored by Overhauser-enhanced MRI with 14N- and $^{15}$N-labeled nitroxyl radicals. *Proc Natl Acad Sci USA* 103: 1463-1468

Woodle M C, Lasic D D (1992) Sterically stabilized liposomes. *Biochim Biophys Acta* 1113: 171-199

Yarden Y (2001) Biology of HER2 and its importance in breast cancer. *Oncology* 61 Suppl 2: 1-13

That which is claimed is:

1. An imaging complex for in vivo electron paramagnetic resonance (EPR) spectroscopic measurements of targeted cellular tissue of interest comprising:
    a liposome;
    a paramagnetic detection probe encapsulated within the liposome, wherein the paramagnetic detection probe is concentrated to a level causing self quenching with no or minimal identifiable signal;
    a targeting ligand positioned on a surface of the liposome and having affinity for a receptor on the targeted cellular tissue of interest; and
    a PEG molecule linking the surface of the liposome to the targeting ligand,
    wherein the paramagnetic detection probe is a nitroxide selected from the group consisting of the following:

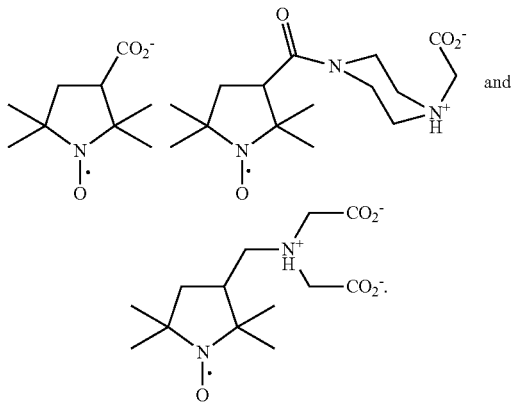

wherein a concentration of the nitroxide encapsulated within the liposome is in a range from about 130 mM to 180 mM and a diameter of the liposome is about 100 nm, and wherein the nitroxide has increased intracellular retention thereby providing an extended time period for obtaining EPR spectroscopic measurements.

2. The imaging complex according to claim 1 wherein the targeting ligand is an antibody or fragment thereof having affinity for the receptor on the targeted cellular tissue of interest.

3. The imaging complex according to claim 1, wherein the nitroxide includes isotopic substitutions and wherein $^{14}$N is replaced with $^{15}$N and $^1$H is replaced with $^2$H (D).

4. A method of diagnosing the presence of diseased tissue/cells in a human or non-human animal, the method comprising:
   a) providing an imaging complex according to claim 1;
   b) administering the imaging complex to the human or non-human animal, wherein the imaging complex is endocytosed and lysed in the targeted tissue/cells to liberate the nitroxide detection probe;
   c) scanning the human or non-human animal using a magnetic field; and
   d) determining the spectral signal of the nitroxide probe loaded into the tissue/cells of interest.

5. The method of claim 4, wherein the targeting ligand is an antibody or fragment thereof having affinity for the receptor on the targeted cellular tissue of interest.

6. An immunoassay method for detecting or quantifying a targeted cellular tissue of interest in a test fluid, said method comprising:
   (a) providing an imaging complex according to claim 1;
   (b) providing a solid phase inert support having attached thereto a support binding receptor having affinity for a second area on the targeted cellular tissue of interest, wherein the support binding receptor has no affinity for the targeting ligand of the imaging complex;
   (c) mixing said test fluid with receptor-solid phase support of step (b) for sufficient time to saturate said support binding receptor with any targeted cellular tissue of interest present in said test fluid;
   (d) mixing said liposome formed in step (a) with saturated receptor-solid phase support from step (c) and for binding with a first area on the targeted cellular tissue of interest;
   (e) causing lysis of said imaging complex; and;
   (f) scanning the solid phase support with a magnetic field to determine the presence of the paramagnetic detection probe released by the imaging complex in step (e), wherein a signal from the scan evidences the presence of the targeted cellular tissue of interest in the sample.

7. The method according to claim 6, wherein the targeting ligand is an antibody or fragment thereof having affinity for the receptor on the targeted cellular tissue of interest.

8. The method according to claim 6, wherein the targeting ligand is an antibody or fragment thereof having affinity for the receptor on the targeted cellular tissue of interest.

* * * * *